US009309556B2

(12) United States Patent
Myllykangas et al.

(10) Patent No.: US 9,309,556 B2
(45) Date of Patent: Apr. 12, 2016

(54) DIRECT CAPTURE, AMPLIFICATION AND SEQUENCING OF TARGET DNA USING IMMOBILIZED PRIMERS

(75) Inventors: Samuel Myllykangas, Espoo (FI); Jason Buenrostro, Redwood City, CA (US); Hanlee P. Ji, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 394 days.

(21) Appl. No.: 13/239,226

(22) Filed: Sep. 21, 2011

(65) Prior Publication Data

US 2012/0157322 A1  Jun. 21, 2012

Related U.S. Application Data

(60) Provisional application No. 61/485,062, filed on May 11, 2011, provisional application No. 61/386,390, filed on Sep. 24, 2010.

(51) Int. Cl.
*C12Q 1/68* (2006.01)
(52) U.S. Cl.
CPC ............ *C12Q 1/6806* (2013.01); *C12Q 1/6837* (2013.01); *C12Q 1/6853* (2013.01); *C12Q 1/6869* (2013.01); *C12Q 1/6874* (2013.01)
(58) Field of Classification Search
None
See application file for complete search history.

(56) References Cited

U.S. PATENT DOCUMENTS

| 2003/0224439 | A1 | 12/2003 | Lafferty et al. | |
| 2005/0191656 | A1 | 9/2005 | Drmanac et al. | |
| 2006/0008824 | A1 | 1/2006 | Ronaghi et al. | |
| 2007/0269817 | A1* | 11/2007 | Shapero ........................... 435/6 |
| 2008/0286795 | A1 | 11/2008 | Kawashima et al. | |
| 2009/0117573 | A1* | 5/2009 | Fu et al. ........................... 435/6 |
| 2009/0117621 | A1 | 5/2009 | Boutell et al. | |
| 2009/0124514 | A1 | 5/2009 | Fu et al. | |
| 2010/0137143 | A1* | 6/2010 | Rothberg et al. ................ 506/2 |

FOREIGN PATENT DOCUMENTS

| JP | 2002503954 | 2/2002 |
| JP | 2003501071 | 1/2003 |
| JP | 2010041985 | 2/2010 |
| WO | WO 2009004335 A1 * | 1/2009 |

OTHER PUBLICATIONS

Shendure, j et al. Next-generation DNA sequencing. Nature Biotechnology, vol. 26, No. 10, p. 1135-1145, 2008.*
Bentley, DR. et al. Accurate whole human genome sequencing using reversible terminator chemistry. Nature, vol. 456, p. 53-59, 2008.*
Albert; et al., "Direct selection of human genomic loci by microarray hybridization", Nature Methods (2007), 4 (11):903-5.
Dahl; et al., "Multigene amplification and massively parallel sequencing for cancer mutation discovery", PNAS (2007), 104(22):9387-9392.
Gnirke; et al., "Solution Hybrid Selection with Ultra-long Oligonucleotides for Massively Parallel Targeted Sequencing", Nat. Biotechnol. (2009), 27(2):182-9.
Hodges; et al., "Genome-wide in situ exon capture for selective resequencing", Nature Genetics (2007), 39:1522-7.
Ley; et al., "DNA sequencing of a cytogenetically normal acute myeloid leukemia genome", Nature (2008), 456 (7218):66-72.
Margulies; et al., "Genome Sequencing in Open Microfabricated High Density Picoliter Reactors", Nature (2005), 437(7057):376-380.
Okou; et al., "Microarray-based genomic selection for highthroughput resequencing", Nature Methods (2007), 4:907-9.
Porreca; et al., "Multiplex amplification of large sets of human exons", Nature Methods (2007), 4:931-6.
Shendure; et al., Accurate Multiplex Polony Sequencing of an Evolved Bacterial Genome, Science (2005), 309:1728-32.
Shendure; et al., "Overview of DNA Sequencing Strategies", Current Protocols in Molecular Biology (2008), 7.1.1-7.1.11.
Turner; et al., "Massively parallel exon capture and library-free resequencing across 16 individuals", Nature Methods (2009), 6(5):315-316.

* cited by examiner

*Primary Examiner* — Prabha Chunduru
(74) *Attorney, Agent, or Firm* — James S. Keddie; Bozicevic, Field & Francis LLP

(57) ABSTRACT

Certain embodiments provide a method for capturing a genomic fragment. The method may comprise: obtaining a substrate comprising a first population of surface-bound oligonucleotides and a second population of surface-bound oligonucleotides; hybridizing a first member of the first population of surface-bound oligonucleotides to a selection oligonucleotide comprising a region that hybridizes with the first member and a region that contains a genomic sequence; extending the first member of the first population of surface-bound oligonucleotides to produce a support-bound selection primer that comprises a sequence that is complementary to the genomic sequence; hybridizing the support-bound selection primer to a nucleic acid fragment comprising the genomic sequence; extending the support-bound selection primer to produce an extension product that contains a sequence that flanks the genomic sequence, e.g., in a genome; and amplifying the extension product on the substrate.

20 Claims, 11 Drawing Sheets

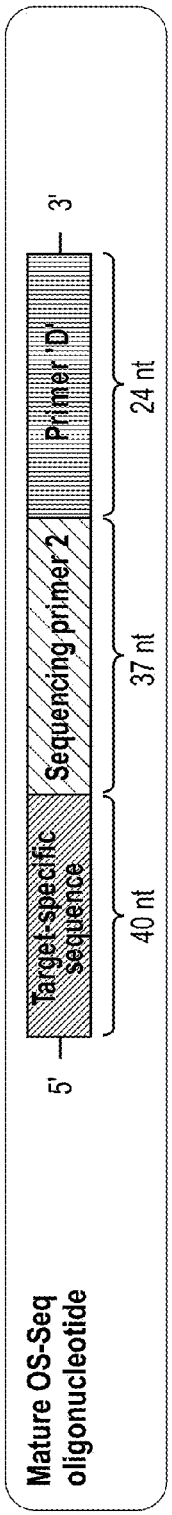
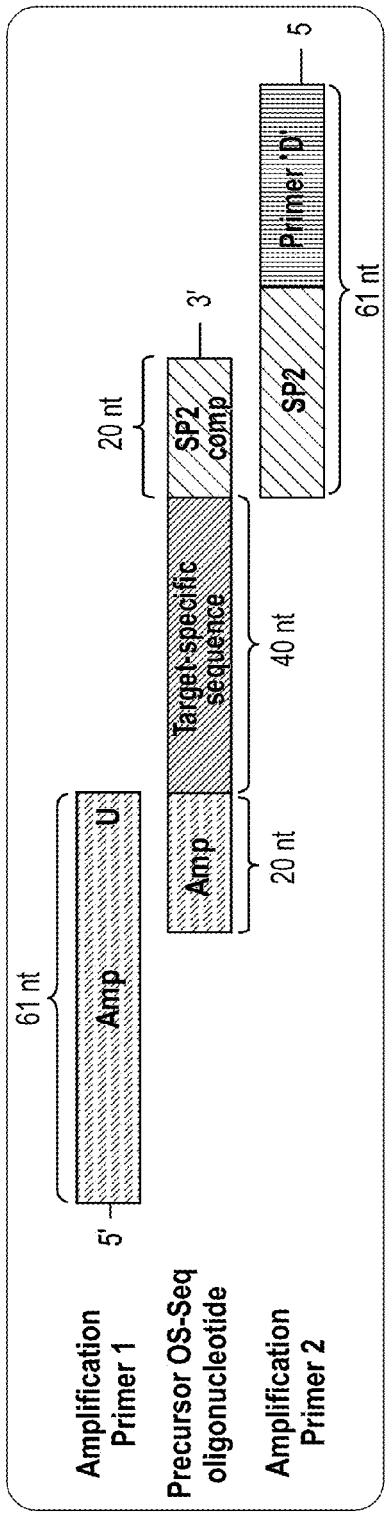
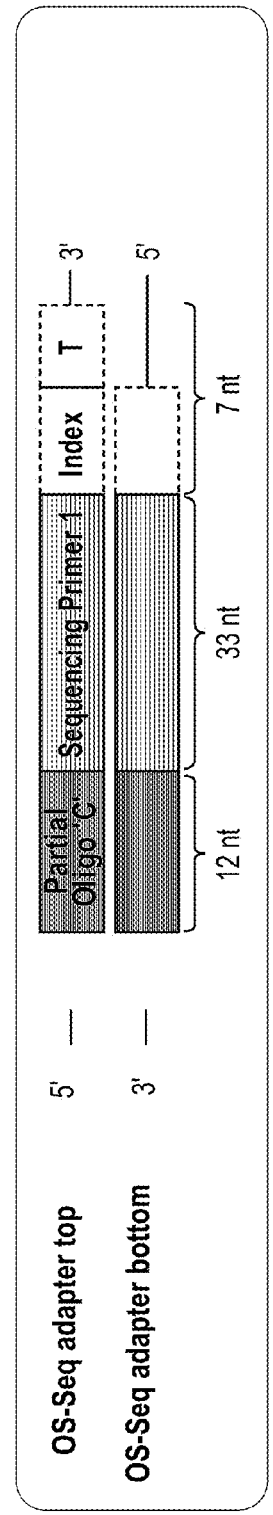
FIG. 5A
FIG. 5B
FIG. 5C

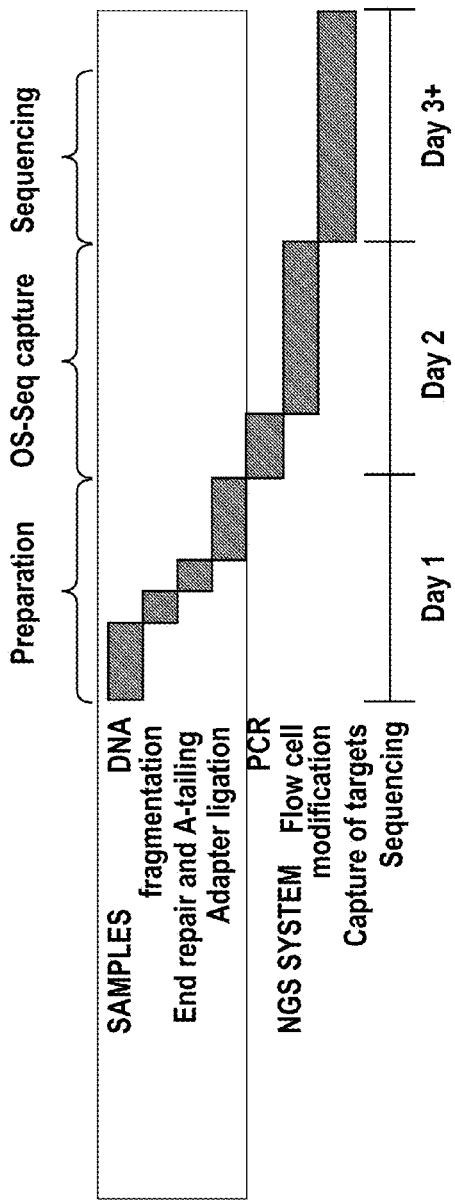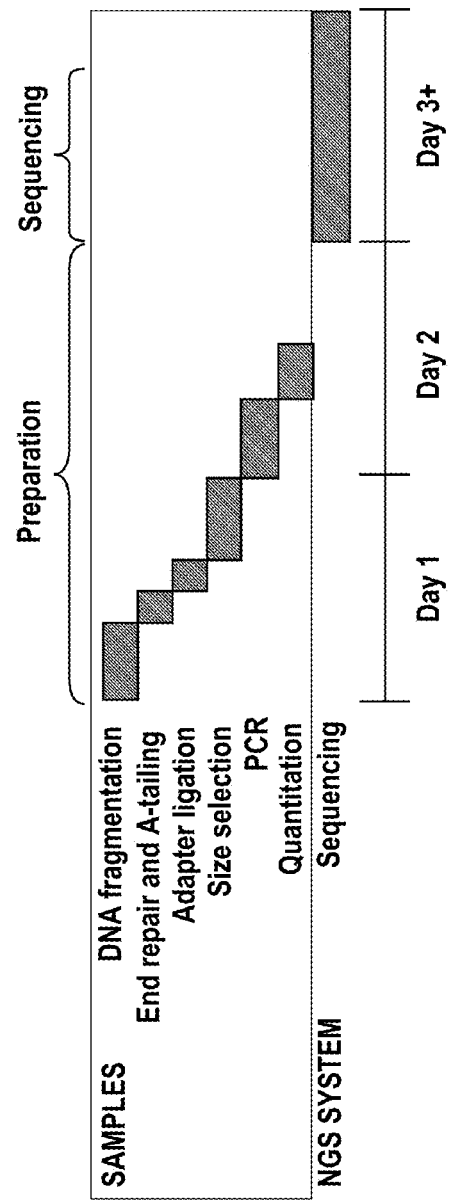

SEQUENCE LISTING

```
<160> NUMBER OF SEQ ID NOS: 83

<210> SEQ ID NO 1
<211> LENGTH: 41
<212> TYPE: DNA
<213> ORGANISM: Artificial Sequence
<220> FEATURE:
<221> NAME/KEY: misc_difference
<222> LOCATION: 40
<223> OTHER INFORMATION: phosphorothioate internucleotide bond
<220> FEATURE:
<223> OTHER INFORMATION: Synthetic oligonucleotide

<400> SEQUENCE: 1
cgagatctac actctttccc tacacgacgc tcttccgatc t                        41

<210> SEQ ID NO 2
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 2
gatcggaaga gcgtcgtgta gggaaagagt gtagatctcg                          40

<210> SEQ ID NO 3
<211> LENGTH: 48
<212> TYPE: DNA
<213> ORGANISM: Artificial Sequence
```

-continued

```
<220> FEATURE:
<221> NAME/KEY: misc_difference
<222> LOCATION: 40
<223> OTHER INFORMATION: phosphorothioate internucleotide bond
<220> FEATURE:
<223> OTHER INFORMATION: Synthetic oligonucleotide

<400> SEQUENCE: 3
cgagatctac actctttccc tacacgacgc tcttccgatc ttgctaat                48

<210> SEQ ID NO 4
<211> LENGTH: 48
<212> TYPE: DNA
<213> ORGANISM: Artificial Sequence
<220> FEATURE:
<221> NAME/KEY: misc_difference
<222> LOCATION: 40
<223> OTHER INFORMATION: phosphorothioate internucleotide bond
<220> FEATURE:
<223> OTHER INFORMATION: Synthetic oligonucleotide

<400> SEQUENCE: 4
cgagatctac actctttccc tacacgacgc tcttccgatc taggtcat                48

<210> SEQ ID NO 5
<211> LENGTH: 48
<212> TYPE: DNA
<213> ORGANISM: Artificial Sequence
<220> FEATURE:
<221> NAME/KEY: misc_difference
<222> LOCATION: 40
<223> OTHER INFORMATION: phosphorothioate internucleotide bond
<220> FEATURE:
<223> OTHER INFORMATION: Synthetic oligonucleotide

<400> SEQUENCE: 5
cgagatctac actctttccc tacacgacgc tcttccgatc tggattat                48

<210> SEQ ID NO 6
<211> LENGTH: 48
<212> TYPE: DNA
<213> ORGANISM: Artificial Sequence
<220> FEATURE:
<221> NAME/KEY: misc_difference
<222> LOCATION: 40
<223> OTHER INFORMATION: phosphorothioate internucleotide bond
<220> FEATURE:
<223> OTHER INFORMATION: Synthetic oligonucleotide

<400> SEQUENCE: 6
cgagatctac actctttccc tacacgacgc tcttccgatc tcgttgat                48

<210> SEQ ID NO 7
<211> LENGTH: 48
<212> TYPE: DNA
<213> ORGANISM: Artificial Sequence
<220> FEATURE:
<221> NAME/KEY: misc_difference
<222> LOCATION: 40
<223> OTHER INFORMATION: phosphorothioate internucleotide bond
<220> FEATURE:
<223> OTHER INFORMATION: Synthetic oligonucleotide

<400> SEQUENCE: 7
cgagatctac actctttccc tacacgacgc tcttccgatc tatgatct                48

<210> SEQ ID NO 8
<211> LENGTH: 48
<212> TYPE: DNA
```

<213> ORGANISM: Artificial Sequence
<220> FEATURE:
<223> OTHER INFORMATION: Synthetic oligonucleotide

<400> SEQUENCE: 8
cgagatctac actctttccc tacacgacgc tcttccgatc tcttaact        48

<210> SEQ ID NO 9
<211> LENGTH: 48
<212> TYPE: DNA
<213> ORGANISM: Artificial Sequence
<220> FEATURE:
<221> NAME/KEY: misc_difference
<222> LOCATION: 40
<223> OTHER INFORMATION: phosphorothioate internucleotide bond
<220> FEATURE:
<223> OTHER INFORMATION: Synthetic oligonucleotide

<400> SEQUENCE: 9
cgagatctac actctttccc tacacgacgc tcttccgatc tttcagct        48

<210> SEQ ID NO 10
<211> LENGTH: 48
<212> TYPE: DNA
<213> ORGANISM: Artificial Sequence
<220> FEATURE:
<221> NAME/KEY: misc_difference
<222> LOCATION: 40
<223> OTHER INFORMATION: phosphorothioate internucleotide bond
<220> FEATURE:
<223> OTHER INFORMATION: Synthetic oligonucleotide

<400> SEQUENCE: 10
cgagatctac actctttccc tacacgacgc tcttccgatc tgtaacct        48

<210> SEQ ID NO 11
<211> LENGTH: 48
<212> TYPE: DNA
<213> ORGANISM: Artificial Sequence
<220> FEATURE:
<221> NAME/KEY: misc_difference
<222> LOCATION: 40
<223> OTHER INFORMATION: phosphorothioate internucleotide bond
<220> FEATURE:
<223> OTHER INFORMATION: Synthetic oligonucleotide

<400> SEQUENCE: 11
cgagatctac actctttccc tacacgacgc tcttccgatc tccaggtt        48

<210> SEQ ID NO 12
<211> LENGTH: 48
<212> TYPE: DNA
<213> ORGANISM: Artificial Sequence
<220> FEATURE:
<221> NAME/KEY: misc_difference
<222> LOCATION: 40
<223> OTHER INFORMATION: phosphorothioate internucleotide bond
<220> FEATURE:
<223> OTHER INFORMATION: Synthetic oligonucleotide

<400> SEQUENCE: 12
cgagatctac actctttccc tacacgacgc tcttccgatc tgccgttt        48

<210> SEQ ID NO 13
<211> LENGTH: 48
<212> TYPE: DNA
<213> ORGANISM: Artificial Sequence
<220> FEATURE:
<221> NAME/KEY: misc_difference

```
<222> LOCATION: 40
<223> OTHER INFORMATION: phosphorothioate internucleotide bond
<220> FEATURE:
<223> OTHER INFORMATION: Synthetic oligonucleotide

<400> SEQUENCE: 13
cgagatctac actctttccc tacacgacgc tcttccgatc tactgctt              48

<210> SEQ ID NO 14
<211> LENGTH: 48
<212> TYPE: DNA
<213> ORGANISM: Artificial Sequence
<220> FEATURE:
<221> NAME/KEY: misc_difference
<222> LOCATION: 40
<223> OTHER INFORMATION: phosphorothioate internucleotide bond
<220> FEATURE:
<223> OTHER INFORMATION: Synthetic oligonucleotide

<400> SEQUENCE: 14
cgagatctac actctttccc tacacgacgc tcttccgatc ttcggatt              48

<210> SEQ ID NO 15
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 15
cgagatctac actctttccc tacacgacgc tcttccgatc tgatccgt              48

<210> SEQ ID NO 16
<211> LENGTH: 48
<212> TYPE: DNA
<213> ORGANISM: Artificial Sequence
<220> FEATURE:
<221> NAME/KEY: misc_difference
<222> LOCATION: 40
<223> OTHER INFORMATION: phosphorothioate internucleotide bond
<220> FEATURE:
<223> OTHER INFORMATION: Synthetic oligonucleotide

<400> SEQUENCE: 16
cgagatctac actctttccc tacacgacgc tcttccgatc ttaacggt              48

<210> SEQ ID NO 17
<211> LENGTH: 48
<212> TYPE: DNA
<213> ORGANISM: Artificial Sequence
<220> FEATURE:
<221> NAME/KEY: misc_difference
<222> LOCATION: 40
<223> OTHER INFORMATION: phosphorothioate internucleotide bond
<220> FEATURE:
<223> OTHER INFORMATION: Synthetic oligonucleotide

<400> SEQUENCE: 17
cgagatctac actctttccc tacacgacgc tcttccgatc tcagcagt              48

<210> SEQ ID NO 18
<211> LENGTH: 48
<212> TYPE: DNA
<213> ORGANISM: Artificial Sequence
<220> FEATURE:
<221> NAME/KEY: misc_difference
<222> LOCATION: 40
<223> OTHER INFORMATION: phosphorothioate internucleotide bond
<220> FEATURE:
```

<223> OTHER INFORMATION: Synthetic oligonucleotide

<400> SEQUENCE: 18
cgagatctac actctttccc tacacgacgc tcttccgatc taacctgt         48

<210> SEQ ID NO 19
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 19
ttagcaagat cggaagagcg tcgtgtaggg aaagagtgta gatctcg         47

<210> SEQ ID NO 20
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 20
tgacctagat cggaagagcg tcgtgtaggg aaagagtgta gatctcg         47

<210> SEQ ID NO 21
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 21
taatccagat cggaagagcg tcgtgtaggg aaagagtgta gatctcg         47

<210> SEQ ID NO 22
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 22
tcaacgagat cggaagagcg tcgtgtaggg aaagagtgta gatctcg         47

<210> SEQ ID NO 23
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 23
gatcatagat cggaagagcg tcgtgtaggg aaagagtgta gatctcg         47

<210> SEQ ID NO 24
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 24
gttaagagat cggaagagcg tcgtgtaggg aaagagtgta gatctcg         47

-continued

<210> SEQ ID NO 25
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 25
gctgaaagat cggaagagcg tcgtgtaggg aaagagtgta gatctcg    47

<210> SEQ ID NO 26
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 26
ggttacagat cggaagagcg tcgtgtaggg aaagagtgta gatctcg    47

<210> SEQ ID NO 27
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 27
acctggagat cggaagagcg tcgtgtaggg aaagagtgta gatctcg    47

<210> SEQ ID NO 28
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 28
aacggcagat cggaagagcg tcgtgtaggg aaagagtgta gatctcg    47

<210> SEQ ID NO 29
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 29
agcagtagat cggaagagcg tcgtgtaggg aaagagtgta gatctcg    47

<210> SEQ ID NO 30
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 30
atccgaagat cggaagagcg tcgtgtaggg aaagagtgta gatctcg    47

<210> SEQ ID NO 31
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 31
cggatcagat cggaagagcg tcgtgtaggg aaagagtgta gatctcg    47

<210> SEQ ID NO 32
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 32
ccgttaagat cggaagagcg tcgtgtaggg aaagagtgta gatctcg    47

<210> SEQ ID NO 33
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 33
ctgctgagat cggaagagcg tcgtgtaggg aaagagtgta gatctcg    47

<210> SEQ ID NO 34
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 34
caggttagat cggaagagcg tcgtgtaggg aaagagtgta gatctcg    47

<210> SEQ ID NO 35
<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 35
gctgacctta aacctaacgc gagggcggca gttgggattt cgtgacctat gcaccagacg    60
u                                                                   61

<210> SEQ ID NO 36
<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 36
caagcagaag acggcatacg agatcggtct cggcattcct gctgaaccgc tcttccgatc    60
t                                                                   61

<210> SEQ ID NO 37
<211> LENGTH: 101
<212> TYPE: DNA
<213> ORGANISM: Artificial Sequence
<220> FEATURE:
<221> NAME/KEY: misc_feature
<222> LOCATION: (1)...(40)
<223> OTHER INFORMATION: n = A,T,C or G
<220> FEATURE:
<223> OTHER INFORMATION: Synthetic oligonucleotide

<400> SEQUENCE: 37
nnnnnnnnnn nnnnnnnnnn nnnnnnnnnn nnnnnnnnnn agatcggaag agcggttcag    60
caggaatgcc gagaccgatc tcgtatgccg tcttctgctt g    101

<210> SEQ ID NO 38
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 38
cgagatctac actctttccc tacacgacgc tcttccgatc t    41

<210> SEQ ID NO 39
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 39
gatcggaaga gcgtcgtgta gggaaagagt gtagatctcg    40

<210> SEQ ID NO 40
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 40
tttttttttt aatgatacgg cgaccaccga gauctacac    39

<210> SEQ ID NO 41
<211> LENGTH: 34
<212> TYPE: DNA
<213> ORGANISM: Artificial Sequence
<220> FEATURE:
<221> NAME/KEY: misc_difference
<222> LOCATION: 32
<223> OTHER INFORMATION: 8-oxoguanine modified base
<220> FEATURE:
<223> OTHER INFORMATION: Synthetic oligonucleotide

<400> SEQUENCE: 41
tttttttttt caagcagaag acggcatacg agat    34

<210> SEQ ID NO 42
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 42
acactctttc cctacacgac gctcttccga tct    33

<210> SEQ ID NO 43
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 43
cggtctcggc attcctgctg aaccgctctt ccgatct                                    37

<210> SEQ ID NO 44
<211> LENGTH: 101
<212> TYPE: DNA
<213> ORGANISM: Artificial Sequence
<220> FEATURE:
<221> NAME/KEY: misc_feature
<222> LOCATION: 62, 63, 64, 65, 66, 67, 68, 69, 70, 71, 72, 73, 74, 75,
      76, 77, 78, 79, 80, 81, 82, 83, 84, 85, 86, 87, 88, 89, 90,
      91, 92, 93, 94, 95, 96, 97, 98, 99, 100, 101
<223> OTHER INFORMATION: n = A,T,C or G
<220> FEATURE:
<223> OTHER INFORMATION: Synthetic oligonucleotide

<400> SEQUENCE: 44
gttcgtcttc tgccgtatgc tctagccaga gccgtaagga cgacttggcg agaaggctag          60
annnnnnnnn nnnnnnnnnn nnnnnnnnnn nnnnnnnnnn n                             101

<210> SEQ ID NO 45
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 45
caagcagaag acggcatacg agat                                                 24

<210> SEQ ID NO 46
<211> LENGTH: 101
<212> TYPE: DNA
<213> ORGANISM: Artificial Sequence
<220> FEATURE:
<221> NAME/KEY: misc_feature
<222> LOCATION: 62, 63, 64, 65, 66, 67, 68, 69, 70, 71, 72, 73, 74, 75,
      76, 77, 78, 79, 80, 81, 82, 83, 84, 85, 86, 87, 88, 89, 90,
      91, 92, 93, 94, 95, 96, 97, 98, 99, 100, 101
<223> OTHER INFORMATION: n = A,T,C or G
<220> FEATURE:
<223> OTHER INFORMATION: Synthetic oligonucleotide

<400> SEQUENCE: 46
gttcgtcttc tgccgtatgc tctagccaga gccgtaagga cgacttggcg agaaggctag          60
annnnnnnnn nnnnnnnnnn nnnnnnnnnn nnnnnnnnnn n                             101

<210> SEQ ID NO 47
<211> LENGTH: 101
<212> TYPE: DNA
<213> ORGANISM: Artificial Sequence
<220> FEATURE:
<221> NAME/KEY: misc_feature
<222> LOCATION: 62, 63, 64, 65, 66, 67, 68, 69, 70, 71, 72, 73, 74, 75,
      76, 77, 78, 79, 80, 81, 82, 83, 84, 85, 86, 87, 88, 89, 90,
      91, 92, 93, 94, 95, 96, 97, 98, 99, 100, 101
<223> OTHER INFORMATION: n = A,T,C or G
<220> FEATURE:
<223> OTHER INFORMATION: Synthetic oligonucleotide

<400> SEQUENCE: 47
caagcagaag acggcatacg agatcggtct cggcattcct gctgaaccgc tcttccgatc          60
tnnnnnnnnn nnnnnnnnnn nnnnnnnnnn nnnnnnnnnn n                             101

<210> SEQ ID NO 48
<211> LENGTH: 101

```
<212> TYPE: DNA
<213> ORGANISM: Artificial Sequence
<220> FEATURE:
<221> NAME/KEY: misc_feature
<222> LOCATION: 62, 63, 64, 65, 66, 67, 68, 69, 70, 71, 72, 73, 74, 75,
      76, 77, 78, 79, 80, 81, 82, 83, 84, 85, 86, 87, 88, 89, 90,
      91, 92, 93, 94, 95, 96, 97, 98, 99, 100, 101
<223> OTHER INFORMATION: n = A,T,C or G
<220> FEATURE:
<223> OTHER INFORMATION: Synthetic oligonucleotide

<400> SEQUENCE: 48
caagcagaag acggcatacg agatcggtct cggcattcct gctgaaccgc tcttccgatc      60
tnnnnnnnnn nnnnnnnnnn nnnnnnnnnn nnnnnnnnnn n                         101

<210> SEQ ID NO 49
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 49
gatcggaaga gcgtcgtgta gggaaagagt gtagatctcg                            40

<210> SEQ ID NO 50
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 50
tctagccttc tcgcagcaca tccctttctc acatctagag c                          41

<210> SEQ ID NO 51
<211> LENGTH: 104
<212> TYPE: DNA
<213> ORGANISM: Artificial Sequence
<220> FEATURE:
<221> NAME/KEY: misc_feature
<222> LOCATION: 42, 43, 44, 45, 46, 47, 48, 49, 50, 51, 52, 53, 54, 55,
      56, 57, 58, 59, 60, 61, 62, 63
<223> OTHER INFORMATION: n = A,T,C or G
<220> FEATURE:
<223> OTHER INFORMATION: Synthetic oligonucleotide

<400> SEQUENCE: 51
cgagatctac actctttccc tacacgacgc tcttccgatc tnnnnnnnnn nnnnnnnnnn      60
nnnagatcgg aagagcgtcg tgtagggaaa gagtgtagat ctcg                       104

<210> SEQ ID NO 52
<211> LENGTH: 104
<212> TYPE: DNA
<213> ORGANISM: Artificial Sequence
<220> FEATURE:
<221> NAME/KEY: misc_feature
<222> LOCATION: 42, 43, 44, 45, 46, 47, 48, 49, 50, 51, 52, 53, 54, 55,
      56, 57, 58, 59, 60, 61, 62, 63
<223> OTHER INFORMATION: n = A,T,C or G
<220> FEATURE:
<223> OTHER INFORMATION: Synthetic oligonucleotide

<400> SEQUENCE: 52
gctctagatg tgagaaaggg atgtgctgcg agaaggctag annnnnnnnn nnnnnnnnnn      60
nnntctagcc ttctcgcagc acatcccttt ctcacatcta gagc                       104
```

<210> SEQ ID NO 53
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 53
cgagatctac actctttccc tacacgacgc tcttccgatc t         41

<210> SEQ ID NO 54
<211> LENGTH: 104
<212> TYPE: DNA
<213> ORGANISM: Artificial Sequence
<220> FEATURE:
<221> NAME/KEY: misc_feature
<222> LOCATION: 42, 43, 44, 45, 46, 47, 48, 49, 50, 51, 52, 53, 54, 55,
      56, 57, 58, 59, 60, 61, 62, 63
<223> OTHER INFORMATION: n = A,T,C or G
<220> FEATURE:
<223> OTHER INFORMATION: Synthetic oligonucleotide

<400> SEQUENCE: 54
gctctagatg tgagaaaggg atgtgctgcg agaaggctag annnnnnnnn nnnnnnnnnn    60
nnntctagcc ttctcgcagc acatcccttt ctcacatcta gagc                   104

<210> SEQ ID NO 55
<211> LENGTH: 104
<212> TYPE: DNA
<213> ORGANISM: Artificial Sequence
<220> FEATURE:
<221> NAME/KEY: misc_feature
<222> LOCATION: 42, 43, 44, 45, 46, 47, 48, 49, 50, 51, 52, 53, 54, 55,
      56, 57, 58, 59, 60, 61, 62, 63
<223> OTHER INFORMATION: n = A,T,C or G
<220> FEATURE:
<223> OTHER INFORMATION: Synthetic oligonucleotide

<400> SEQUENCE: 55
cgagatctac actctttccc tacacgacgc tcttccgatc tnnnnnnnnn nnnnnnnnnn    60
nnnagatcgg aagagcgtcg tgtagggaaa gagtgtagat ctcg                   104

<210> SEQ ID NO 56
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 56
tctagccttc tcgcagcaca tccctttctc acatctagag c         41

<210> SEQ ID NO 57
<211> LENGTH: 104
<212> TYPE: DNA
<213> ORGANISM: Artificial Sequence
<220> FEATURE:
<221> NAME/KEY: misc_feature
<222> LOCATION: 42, 43, 44, 45, 46, 47, 48, 49, 50, 51, 52, 53, 54, 55,
      56, 57, 58, 59, 60, 61, 62, 63
<223> OTHER INFORMATION: n = A,T,C or G
<220> FEATURE:
<223> OTHER INFORMATION: Synthetic oligonucleotide

<400> SEQUENCE: 57
cgagatctac actctttccc tacacgacgc tcttccgatc tnnnnnnnnn nnnnnnnnnn    60

```
nnnagatcgg aagagcgtcg tgtagggaaa gagtgtagat ctcg                      104
```

<210> SEQ ID NO 58
<211> LENGTH: 104
<212> TYPE: DNA
<213> ORGANISM: Artificial Sequence
<220> FEATURE:
<221> NAME/KEY: misc_feature
<222> LOCATION: 42, 43, 44, 45, 46, 47, 48, 49, 50, 51, 52, 53, 54, 55,
      56, 57, 58, 59, 60, 61, 62, 63
<223> OTHER INFORMATION: n = A,T,C or G
<220> FEATURE:
<223> OTHER INFORMATION: Synthetic oligonucleotide

<400> SEQUENCE: 58

```
gctctagatg tgagaaaggg atgtgctgcg agaaggctag annnnnnnnn nnnnnnnnn      60 nnntctagcc ttctcgcagc acatcccttt ctcacatcta gagc                     104
```

<210> SEQ ID NO 59
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 59

```
gctctagatg tgagaaaggg atgtgctgcg agaaggctag a                         41
```

<210> SEQ ID NO 60
<211> LENGTH: 81
<212> TYPE: DNA
<213> ORGANISM: Artificial Sequence
<220> FEATURE:
<221> NAME/KEY: misc_feature
<222> LOCATION: 1, 2, 3, 4, 5, 6, 7, 8, 9, 10, 11, 12, 13, 14, 15, 16,
      17, 18, 19, 20, 21, 22, 23, 24, 25, 26, 27, 28, 29, 30, 31,
      32, 33, 34, 35, 36, 37, 38, 39, 40
<223> OTHER INFORMATION: n = A,T,C or G
<220> FEATURE:
<223> OTHER INFORMATION: Synthetic oligonucleotide

<400> SEQUENCE: 60

```
nnnnnnnnnn nnnnnnnnnn nnnnnnnnnn nnnnnnnnnn tctagccttc tcgcagcaca     60
tccctttctc acatctagag c                                               81
```

<210> SEQ ID NO 61
<211> LENGTH: 101
<212> TYPE: DNA
<213> ORGANISM: Artificial Sequence
<220> FEATURE:
<221> NAME/KEY: misc_feature
<222> LOCATION: 62, 63, 64, 65, 66, 67, 68, 69, 70, 71, 72, 73, 74, 75,
      76, 77, 78, 79, 80, 81, 82, 83, 84, 85, 86, 87, 88, 89, 90,
      91, 92, 93, 94, 95, 96, 97, 98, 99, 100, 101
<223> OTHER INFORMATION: n = A,T,C or G
<220> FEATURE:
<223> OTHER INFORMATION: Synthetic oligonucleotide

<400> SEQUENCE: 61

```
caagcagaag acggcatacg agatcggtct cggcattcct gctgaaccgc tcttccgatc     60
tnnnnnnnnn nnnnnnnnnn nnnnnnnnnn nnnnnnnnnn n                        101
```

<210> SEQ ID NO 62
<211> LENGTH: 41
<212> TYPE: DNA
<213> ORGANISM: Artificial Sequence
<220> FEATURE:

<223> OTHER INFORMATION: Synthetic oligonucleotide

<400> SEQUENCE: 62
gctctagatg tgagaaaggg atgtgctgcg agaaggctag a                41

<210> SEQ ID NO 63
<211> LENGTH: 81
<212> TYPE: DNA
<213> ORGANISM: Artificial Sequence
<220> FEATURE:
<221> NAME/KEY: misc_feature
<222> LOCATION: 1, 2, 3, 4, 5, 6, 7, 8, 9, 10, 11, 12, 13, 14, 15, 16,
      17, 18, 19, 20, 21, 22, 23, 24, 25, 26, 27, 28, 29, 30, 31,
      32, 33, 34, 35, 36, 37, 38, 39, 40
<223> OTHER INFORMATION: n = A,T,C or G
<220> FEATURE:
<223> OTHER INFORMATION: Synthetic oligonucleotide

<400> SEQUENCE: 63
nnnnnnnnnn nnnnnnnnnn nnnnnnnnnn nnnnnnnnnn tctagccttc tcgcagcaca    60
tccctttctc acatctagag c                                               81

<210> SEQ ID NO 64
<211> LENGTH: 142
<212> TYPE: DNA
<213> ORGANISM: Artificial Sequence
<220> FEATURE:
<221> NAME/KEY: misc_feature
<222> LOCATION: 62, 63, 64, 65, 66, 67, 68, 69, 70, 71, 72, 73, 74, 75,
      76, 77, 78, 79, 80, 81, 82, 83, 84, 85, 86, 87, 88, 89, 90,
      91, 92, 93, 94, 95, 96, 97, 98, 99, 100, 101
<223> OTHER INFORMATION: n = A,T,C or G
<220> FEATURE:
<223> OTHER INFORMATION: Synthetic oligonucleotide

<400> SEQUENCE: 64
caagcagaag acggcatacg agatcggtct cggcattcct gctgaaccgc tcttccgatc    60
tnnnnnnnnn nnnnnnnnnn nnnnnnnnnn nnnnnnnnnn nagatcggaa gagcgtcgtg   120
tagggaaaga gtgtagatct cg                                              142

<210> SEQ ID NO 65
<211> LENGTH: 142
<212> TYPE: DNA
<213> ORGANISM: Artificial Sequence
<220> FEATURE:
<221> NAME/KEY: misc_feature
<222> LOCATION: 62, 63, 64, 65, 66, 67, 68, 69, 70, 71, 72, 73, 74, 75,
      76, 77, 78, 79, 80, 81, 82, 83, 84, 85, 86, 87, 88, 89, 90,
      91, 92, 93, 94, 95, 96, 97, 98, 99, 100, 101
<223> OTHER INFORMATION: n = A,T,C or G
<220> FEATURE:
<223> OTHER INFORMATION: Synthetic oligonucleotide

<400> SEQUENCE: 65
caagcagaag acggcatacg agatcggtct cggcattcct gctgaaccgc tcttccgatc    60
tnnnnnnnnn nnnnnnnnnn nnnnnnnnnn nnnnnnnnnn nagatcggaa gagcgtcgtg   120
tagggaaaga gtgtagatct cg                                              142

<210> SEQ ID NO 66
<211> LENGTH: 142
<212> TYPE: DNA
<213> ORGANISM: Artificial Sequence
<220> FEATURE:
<221> NAME/KEY: misc_feature
<222> LOCATION: 62, 63, 64, 65, 66, 67, 68, 69, 70, 71, 72, 73, 74, 75,
      76, 77, 78, 79, 80, 81, 82, 83, 84, 85, 86, 87, 88, 89, 90,

```
                               91, 92, 93, 94, 95, 96, 97, 98, 99, 100, 101
<223> OTHER INFORMATION: n = A,T,C or G
<220> FEATURE:
<223> OTHER INFORMATION: Synthetic oligonucleotide

<400> SEQUENCE: 66
caagcagaag acggcatacg agatcggtct cggcattcct gctgaaccgc tcttccgatc    60
tnnnnnnnnn nnnnnnnnnn nnnnnnnnnn nnnnnnnnnn nagatcggaa gagcgtcgtg   120
tagggaaaga gtgtagatct cg                                            142

<210> SEQ ID NO 67
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 67
cacatctaga gccaccagcg gcatagtaa                                      29

<210> SEQ ID NO 68
<211> LENGTH: 159
<212> TYPE: DNA
<213> ORGANISM: Artificial Sequence
<220> FEATURE:
<221> NAME/KEY: misc_feature
<222> LOCATION: 62, 63, 64, 65, 66, 67, 68, 69, 70, 71, 72, 73, 74, 75,
      76, 77, 78, 79, 80, 81, 82, 83, 84, 85, 86, 87, 88, 89, 90,
      91, 92, 93, 94, 95, 96, 97, 98, 99, 100, 101
<223> OTHER INFORMATION: n = A,T,C or G
<220> FEATURE:
<223> OTHER INFORMATION: Synthetic oligonucleotide

<400> SEQUENCE: 68
caagcagaag acggcatacg agatcggtct cggcattcct gctgaaccgc tcttccgatc    60
tnnnnnnnnn nnnnnnnnnn nnnnnnnnnn nnnnnnnnnn nagatcggaa gagcgtcgtg   120
tagggaaaga gtgtagatct cggtggtcgc cgtatcatt                          159

<210> SEQ ID NO 69
<211> LENGTH: 159
<212> TYPE: DNA
<213> ORGANISM: Artificial Sequence
<220> FEATURE:
<221> NAME/KEY: misc_feature
<222> LOCATION: 62, 63, 64, 65, 66, 67, 68, 69, 70, 71, 72, 73, 74, 75,
      76, 77, 78, 79, 80, 81, 82, 83, 84, 85, 86, 87, 88, 89, 90,
      91, 92, 93, 94, 95, 96, 97, 98, 99, 100, 101
<223> OTHER INFORMATION: n = A,T,C or G
<220> FEATURE:
<223> OTHER INFORMATION: Synthetic oligonucleotide

<400> SEQUENCE: 69
gttcgtcttc tgccgtatgc tctagccaga gccgtaagga cgacttggcg agaaggctag    60
annnnnnnnn nnnnnnnnnn nnnnnnnnnn nnnnnnnnnn ntctagcctt ctcgcagcac   120
atccctttct cacatctaga gccaccagcg gcatagtaa                          159

<210> SEQ ID NO 70
<211> LENGTH: 159
<212> TYPE: DNA
<213> ORGANISM: Artificial Sequence
<220> FEATURE:
<221> NAME/KEY: misc_feature
<222> LOCATION: 62, 63, 64, 65, 66, 67, 68, 69, 70, 71, 72, 73, 74, 75,
      76, 77, 78, 79, 80, 81, 82, 83, 84, 85, 86, 87, 88, 89, 90,
      91, 92, 93, 94, 95, 96, 97, 98, 99, 100, 101
```

```
<223> OTHER INFORMATION: n = A,T,C or G
<220> FEATURE:
<223> OTHER INFORMATION: Synthetic oligonucleotide

<400> SEQUENCE: 70
caagcagaag acggcatacg agatcggtct cggcattcct gctgaaccgc tcttccgatc        60
tnnnnnnnnn nnnnnnnnnn nnnnnnnnnn nnnnnnnnnn nagatcggaa gagcgtcgtg       120
tagggaaaga gtgtagatct cggtggtcgc cgtatcatt                              159

<210> SEQ ID NO 71
<211> LENGTH: 159
<212> TYPE: DNA
<213> ORGANISM: Artificial Sequence
<220> FEATURE:
<221> NAME/KEY: misc_feature
<222> LOCATION: 62, 63, 64, 65, 66, 67, 68, 69, 70, 71, 72, 73, 74, 75,
      76, 77, 78, 79, 80, 81, 82, 83, 84, 85, 86, 87, 88, 89, 90,
      91, 92, 93, 94, 95, 96, 97, 98, 99, 100, 101
<223> OTHER INFORMATION: n = A,T,C or G
<220> FEATURE:
<223> OTHER INFORMATION: Synthetic oligonucleotide

<400> SEQUENCE: 71
gttcgtcttc tgccgtatgc tctagccaga gccgtaagga cgacttggcg agaaggctag        60
annnnnnnnn nnnnnnnnnn nnnnnnnnnn nnnnnnnnnn ntctagcctt ctcgcagcac       120
atccctttct cacatctaga gccaccagcg gcatagtaa                              159

<210> SEQ ID NO 72
<211> LENGTH: 159
<212> TYPE: DNA
<213> ORGANISM: Artificial Sequence
<220> FEATURE:
<221> NAME/KEY: misc_feature
<222> LOCATION: 62, 63, 64, 65, 66, 67, 68, 69, 70, 71, 72, 73, 74, 75,
      76, 77, 78, 79, 80, 81, 82, 83, 84, 85, 86, 87, 88, 89, 90,
      91, 92, 93, 94, 95, 96, 97, 98, 99, 100, 101
<223> OTHER INFORMATION: n = A,T,C or G
<220> FEATURE:
<223> OTHER INFORMATION: Synthetic oligonucleotide

<400> SEQUENCE: 72
caagcagaag acggcatacg agatcggtct cggcattcct gctgaaccgc tcttccgatc        60
tnnnnnnnnn nnnnnnnnnn nnnnnnnnnn nnnnnnnnnn nagatcggaa gagcgtcgtg       120
tagggaaaga gtgtagatct cggtggtcgc cgtatcatt                              159

<210> SEQ ID NO 73
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 73
cacatctaga gccaccagcg gcatagtaa                                          29

<210> SEQ ID NO 74
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 74
caagcagaag acggcatacg agat                                               24
```

```
<210> SEQ ID NO 75
<211> LENGTH: 159
<212> TYPE: DNA
<213> ORGANISM: Artificial Sequence
<220> FEATURE:
<221> NAME/KEY: misc_feature
<222> LOCATION: 62, 63, 64, 65, 66, 67, 68, 69, 70, 71, 72, 73, 74, 75,
      76, 77, 78, 79, 80, 81, 82, 83, 84, 85, 86, 87, 88, 89, 90,
      91, 92, 93, 94, 95, 96, 97, 98, 99, 100, 101
<223> OTHER INFORMATION: n = A,T,C or G
<220> FEATURE:
<223> OTHER INFORMATION: Synthetic oligonucleotide

<400> SEQUENCE: 75
gttcgtcttc tgccgtatgc tctagccaga gccgtaagga cgacttggcg agaaggctag      60
annnnnnnnn nnnnnnnnnn nnnnnnnnnn nnnnnnnnnn ntctagcctt ctcgcagcac     120
atcccttcct cacatctaga gccaccagcg gcatagtaa                            159

<210> SEQ ID NO 76
<211> LENGTH: 159
<212> TYPE: DNA
<213> ORGANISM: Artificial Sequence
<220> FEATURE:
<221> NAME/KEY: misc_feature
<222> LOCATION: 62, 63, 64, 65, 66, 67, 68, 69, 70, 71, 72, 73, 74, 75,
      76, 77, 78, 79, 80, 81, 82, 83, 84, 85, 86, 87, 88, 89, 90,
      91, 92, 93, 94, 95, 96, 97, 98, 99, 100, 101
<223> OTHER INFORMATION: n = A,T,C or G
<220> FEATURE:
<223> OTHER INFORMATION: Synthetic oligonucleotide

<400> SEQUENCE: 76
caagcagaag acggcatacg agatcggtct cggcattcct gctgaaccgc tcttccgatc      60
tnnnnnnnnn nnnnnnnnnn nnnnnnnnnn nnnnnnnnnn nagatcggaa gagcgtcgtg     120
tagggaaaga gtgtagatct cggtggtcgc cgtatcatt                            159

<210> SEQ ID NO 77
<211> LENGTH: 159
<212> TYPE: DNA
<213> ORGANISM: Artificial Sequence
<220> FEATURE:
<221> NAME/KEY: misc_feature
<222> LOCATION: 62, 63, 64, 65, 66, 67, 68, 69, 70, 71, 72, 73, 74, 75,
      76, 77, 78, 79, 80, 81, 82, 83, 84, 85, 86, 87, 88, 89, 90,
      91, 92, 93, 94, 95, 96, 97, 98, 99, 100, 101
<223> OTHER INFORMATION: n = A,T,C or G
<220> FEATURE:
<223> OTHER INFORMATION: Synthetic oligonucleotide

<400> SEQUENCE: 77
gttcgtcttc tgccgtatgc tctagccaga gccgtaagga cgacttggcg agaaggctag      60
annnnnnnnn nnnnnnnnnn nnnnnnnnnn nnnnnnnnnn ntctagcctt ctcgcagcac     120
atcccttcct cacatctaga gccaccagcg gcatagtaa                            159

<210> SEQ ID NO 78
<211> LENGTH: 159
<212> TYPE: DNA
<213> ORGANISM: Artificial Sequence
<220> FEATURE:
<221> NAME/KEY: misc_feature
<222> LOCATION: 62, 63, 64, 65, 66, 67, 68, 69, 70, 71, 72, 73, 74, 75,
      76, 77, 78, 79, 80, 81, 82, 83, 84, 85, 86, 87, 88, 89, 90,
      91, 92, 93, 94, 95, 96, 97, 98, 99, 100, 101
<223> OTHER INFORMATION: n = A,T,C or G
<220> FEATURE:
```

<223> OTHER INFORMATION: Synthetic oligonucleotide

<400> SEQUENCE: 78
caagcagaag acggcatacg agatcggtct cggcattcct gctgaaccgc tcttccgatc   60
tnnnnnnnnn nnnnnnnnnn nnnnnnnnnn nnnnnnnnnn nagatcggaa gagcgtcgtg   120
tagggaaaga gtgtagatct cggtggtcgc cgtatcatt   159

<210> SEQ ID NO 79
<211> LENGTH: 159
<212> TYPE: DNA
<213> ORGANISM: Artificial Sequence
<220> FEATURE:
<221> NAME/KEY: misc_feature
<222> LOCATION: 62, 63, 64, 65, 66, 67, 68, 69, 70, 71, 72, 73, 74, 75,
      76, 77, 78, 79, 80, 81, 82, 83, 84, 85, 86, 87, 88, 89, 90,
      91, 92, 93, 94, 95, 96, 97, 98, 99, 100, 101
<223> OTHER INFORMATION: n = A,T,C or G
<220> FEATURE:
<223> OTHER INFORMATION: Synthetic oligonucleotide

<400> SEQUENCE: 79
gttcgtcttc tgccgtatgc tctagccaga gccgtaagga cgacttggcg agaaggctag   60
annnnnnnnn nnnnnnnnnn nnnnnnnnnn nnnnnnnnnn ntctagcctt ctcgcagcac   120
atccctttct cacatctaga gccaccagcg gcatagtaa   159

<210> SEQ ID NO 80
<211> LENGTH: 159
<212> TYPE: DNA
<213> ORGANISM: Artificial Sequence
<220> FEATURE:
<221> NAME/KEY: misc_feature
<222> LOCATION: 62, 63, 64, 65, 66, 67, 68, 69, 70, 71, 72, 73, 74, 75,
      76, 77, 78, 79, 80, 81, 82, 83, 84, 85, 86, 87, 88, 89, 90,
      91, 92, 93, 94, 95, 96, 97, 98, 99, 100, 101
<223> OTHER INFORMATION: n = A,T,C or G
<220> FEATURE:
<223> OTHER INFORMATION: Synthetic oligonucleotide

<400> SEQUENCE: 80
caagcagaag acggcatacg agatcggtct cggcattcct gctgaaccgc tcttccgatc   60
tnnnnnnnnn nnnnnnnnnn nnnnnnnnnn nnnnnnnnnn nagatcggaa gagcgtcgtg   120
tagggaaaga gtgtagatct cggtggtcgc cgtatcatt   159

<210> SEQ ID NO 81
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 81
tctagccttc tcgcagcaca tccctttctc aca   33

<210> SEQ ID NO 82
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 82
cggtctcggc attcctgctg aaccgctctt ccgatct   37

```
-continued

<210> SEQ ID NO 83
<211> LENGTH: 159
<212> TYPE: DNA
<213> ORGANISM: Artificial Sequence
<220> FEATURE:
<221> NAME/KEY: misc_feature
<222> LOCATION: 62, 63, 64, 65, 66, 67, 68, 69, 70, 71, 72, 73, 74, 75,
      76, 77, 78, 79, 80, 81, 82, 83, 84, 85, 86, 87, 88, 89, 90,
      91, 92, 93, 94, 95, 96, 97, 98, 99, 100, 101
<223> OTHER INFORMATION: n = A,T,C or G
<220> FEATURE:
<223> OTHER INFORMATION: Synthetic oligonucleotide

<400> SEQUENCE: 83
gttcgtcttc tgccgtatgc tctagccaga gccgtaagga cgacttggcg agaaggctag      60
annnnnnnnn nnnnnnnnnn nnnnnnnnnn nnnnnnnnnn ntctagcctt ctcgcagcac     120 atcccttct cacatctaga gccaccagcg gcatagtaa                             159
```

DIRECT CAPTURE, AMPLIFICATION AND SEQUENCING OF TARGET DNA USING IMMOBILIZED PRIMERS

CROSS-REFERENCING

This application claims the benefit of U.S. provisional patent application Ser. Nos. 61/386,390, filed on Sep. 24, 2010, and 61/485,062 filed on May 11, 2011, which applications are incorporated herein in their entirety

GOVERNMENT RIGHTS

This invention was made with Government support under contract HG000205 awarded by the National Institutes of Health. The Government has certain rights in this invention.

BACKGROUND

In many sequencing methods, particularly re-sequencing methods (i.e., methods in which a locus is re-sequenced), a target is first captured and then sequenced. Several target capture methodologies have been developed and integrated with high throughput sequencing systems. Specifically, hybridization-based assays using beads or microarrays and in-solution based techniques using molecular inversion probes or genomic circularization oligonucleotides can be applied to capture target DNA. Captured DNA is then prepared for sequencing. Complicated molecular biology protocols are often employed to prepare the enriched DNA sample and in certain cases production of the sequencing library involves many enzymatic reactions, purification steps and size selection by gel electrophoresis. The sample preparation process for target capture DNA sequencing can be labor intensive and subsequent sample manipulations can cause bias in the DNA content and increase the sequencing error rate.

SUMMARY

Provided herein are methods for capturing and amplifying a nucleic acid fragment, e.g., a genomic fragment or cDNA made from RNA. Kits for practicing the method are also provided. In certain embodiments, the method comprises: a) obtaining a substrate comprising a first population of surface-bound oligonucleotides and a second population of surface-bound oligonucleotides, wherein the members of the first and second populations of surface-bound oligonucleotides are not spatially addressed on the substrate; b) hybridizing a first member of the first population of surface-bound oligonucleotides to a selection oligonucleotide comprising a region that hybridizes with the first member and a region that contains a genomic sequence, c) extending the first member of the first population of surface-bound oligonucleotides to produce a support-bound selection primer that comprises a sequence that is complementary to the genomic sequence; d) hybridizing the support-bound selection primer to a nucleic acid fragment (e.g., a genomic fragment or cDNA) comprising the genomic sequence; e) extending the support-bound selection primer to produce an extension product that contains a sequence that flanks the genomic sequence, e.g., in the genome; f) amplifying the extension product on the substrate, e.g., by bridge PCR using unextended members of the first and second populations of surface-bound oligonucleotides, to produce a PCR product.

In certain embodiments, the method comprises: a) obtaining a substrate comprising a first population of surface-bound oligonucleotides and a second population of surface-bound oligonucleotides, wherein the first and second populations of surface-bound oligonucleotides are not spatially addressed on the substrate; b) hybridizing a first member of the first population of surface-bound oligonucleotides to a selection oligonucleotide comprising a region that hybridizes with the first member and a region that contains a genomic sequence; c) extending the first member of the first population of surface-bound oligonucleotides to produce a support-bound selection primer that comprises a sequence that is complementary to the genomic sequence; d) hybridizing the support-bound selection primer to a nucleic acid fragment comprising the genomic sequence; e) extending the support-bound selection primer to produce an extension product that contains a sequence that flanks the genomic sequence, e.g., in a genome; and f) amplifying the extension product, e.g., using bridge PCR on the substrate to produce a PCR product.

Depending on how the method is implemented, an adaptor may be either ligated to the genomic fragment prior to hybridization, or to the extension product after the support bound selection primer is extended. The distal adaptor may hybridize to a surface bound oligonucleotide (which may itself be an extension product produced by a templated extension of the second population of surface-bound oligonucleotides), thereby allowing bridge PCR to occur. The selection primer may also contain a sequencing primer binding site that can be employed to sequence the PCR product.

The method described above generally finds use in resequencing methods in which the sequence of a reference locus is available and the same locus is to be resequenced in a plurality of test samples. In this utility, a selection oligonucleotide is designed to hybridize to an oligonucleotide on the substrate and a region that flanks the locus to be resequenced. The locus is captured on the substrate and then amplified prior to sequencing. For example, a single locus or multiple different loci (e.g., up to 10, 50, 100, 200 or 1,000 or more loci) may be captured from a sample that is made from one individual or multiple individuals (e.g., up to 10, 50, 100, 200 or 1,000 or more individuals).

In certain embodiments, the method comprises: a) obtaining a substrate comprising a first population of surface-bound oligonucleotides and a second population of surface-bound oligonucleotides, wherein the first and second populations of surface-bound oligonucleotides are randomly interspersed on the substrate and not spatially addressed; b) hybridizing a first member of the first population of surface-bound oligonucleotides to a selection oligonucleotide comprising a region that hybridizes with the first member and a region that contains a genomic sequence; c) extending the first member of the first population of surface-bound oligonucleotides to produce a support-bound selection primer that comprises a sequence that is complementary to the genomic sequence; d) hybridizing the support-bound selection primer to an adaptor-ligated fragment (e.g., an adaptor-ligated genomic fragment) comprising the genomic sequence; e) extending the support-bound selection primer to produce a product that contains a sequence that flanks the genomic sequence (e.g., in a genome) and the sequence of the adaptor of the adaptor-ligated genomic fragment; and f) amplifying the product using bridge PCR to produce a PCR product.

In alternative embodiments, the method may comprise: a) obtaining a substrate comprising a first population of surface-bound oligonucleotides and a second population of surface-bound oligonucleotides, wherein the first and second populations of surface-bound oligonucleotides are randomly interspersed on the substrate and not spatially addressed; b) hybridizing a first member of the first population of surface-bound oligonucleotides to a selection oligonucleotide comprising a region that hybridizes with the first member and a region that contains a genomic sequence; c) extending the first member of the first population of surface-bound oligonucleotides to produce a support-bound selection primer that comprises a sequence that is complementary to the genomic sequence; e) extending the support-bound selection primer to produce a product that contains a sequence that flanks the genomic sequence; f) ligating a double stranded adapter onto the product to produce an adaptor modified product; and g) amplifying the adaptor-modified product using bridge PCR to produce a PCR product.

In particular cases, the method may further comprise: i. ligating the genomic fragments to an adaptor that contains a site for a sequencing primer and a nucleotide sequence that is the same as the second surface bound oligonucleotides, ii. hybridizing the adaptor-ligated genomic fragments to a first member of the first population of surface-bound oligonucleotides, ii. extending the first member of the first population of surface-bound oligonucleotides to which the adaptor ligated fragment is hybridized; and iv. hybridizing the adaptor-containing end of the extension product to a second support bound polynucleotide, thereby producing a bridge and facilitating bridge PCR.

BRIEF DESCRIPTION OF THE FIGURES

Certain aspects of the following detailed description are best understood when read in conjunction with the accompanying drawings. It is emphasized that, according to common practice, the various features of the drawings are not to scale. On the contrary, the dimensions of the various features are arbitrarily expanded or reduced for clarity. Included in the drawings are the following figures:

FIG. 5. Structures of oligonucleotide components in OS-Seq. (a) Mature 101-mer OS-Seq oligonucleotides contained target-specific site and sequences encoding for sequencing primer 2 and flow cell primer 'D'. (b) Microarray-synthesized oligonucleotides were amplified using primers that incorporated Uracil to the 5' end of the OS-Seq oligonucleotide and additional active sites for sequencing. (c) Adapter for OS-Seq contained T-overhang for sticky-end ligation to the A-tailed genomic fragments. In addition, indexing sequences as well as flow cell primer 'C' site were present in the dsDNA adapter.

FIG. 9A-B. Comparison of the processing workflow for OS-Seq and shotgun library creation methods.

DEFINITIONS

Figure 1A:
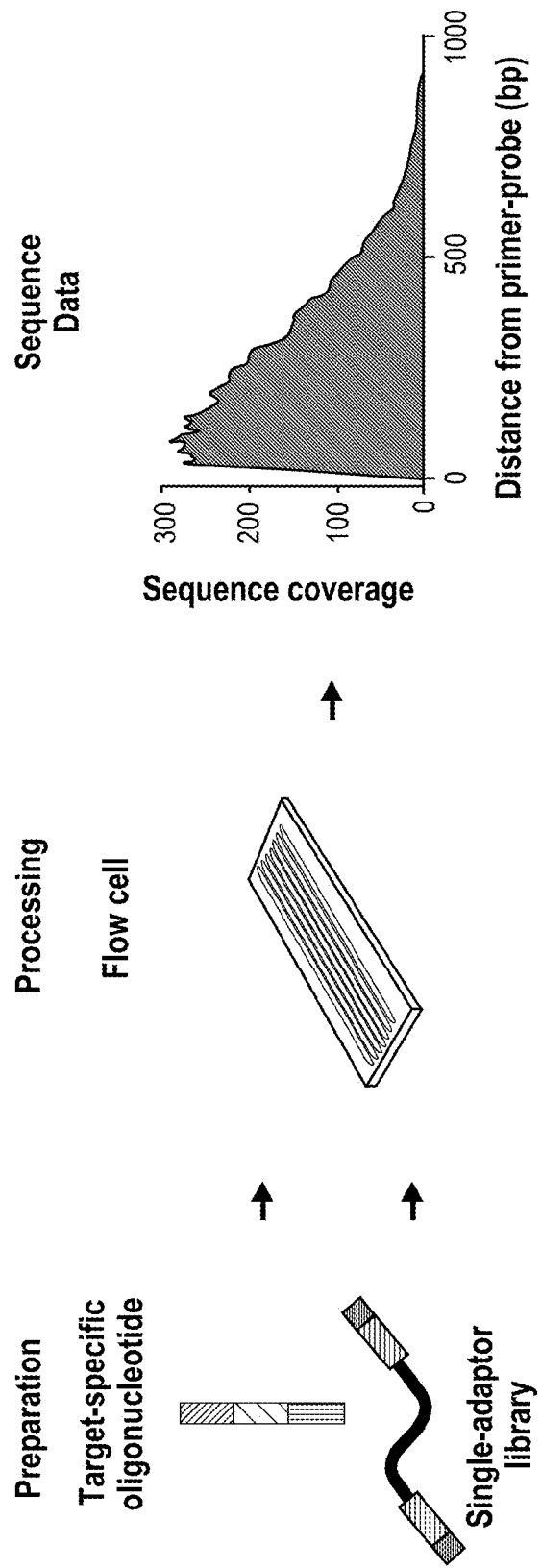
FIG. 1. An overview of the one embodiment of the subject method called "OS-Seq". (a) OS-Seq is a targeted resequencing method that is seamlessly integrated with the Illumina NGS platform. Target-specific oligonucleotides, a sequencing library and an Illumina cluster generation kit are needed for this method. Capture of targets, processing and sequencing are performed on the NGS system. Data originating from each primer-probe is targeted and strand-specific. Shown here is the median coverage profile for OS-Seq-366. (b) Processing of OS-Seq involves three steps of hybridization, DNA polymerase-mediated extension and DNA denaturation. Step 1; Target-specific oligonucleotides are used to modify flow cell primers to primer-probes. In the Illumina sequencing system two types of primers (named C and D) are immobilized on a paired-end flow cell. In OS-Seq a subset of D primers are modified to primer-probes using complex library of oligonucleotides. Oligonucleotides have sequences that hybridize to type D flow cell primers. Hybridized oligonucleotides are then used as a template for DNA polymerase and D primers are extended. After denaturation, target-specific primer-probes are randomly immobilized on the flow cell. Step 2: Genomic targets in a single-adaptor library are captured using primer-probes. Sample preparation for Illumina sequencing involves the addition of specific DNA adapters to the genomic DNA fragments. These adapters incorporate sites for sequencing primers and immobilized flow cell primers. In OS-Seq, we use a modified adapter to prepare single-adapter libraries from genomic DNA. Targets in single-adaptor library are captured during high heat hybridization to their complementary primer-probes. Captured single-adapter library fragments are used as a template for DNA polymerase and primer-probes are extended. Denaturation releases template DNA from immobilized targets. Step 3: Immobilized targets are rendered to be compatible with Illumina sequencing. In Illumina sequencing, solid-phase amplification of the immobilized sequencing library fragments using C and D primers is required. In OS-Seq, during low heat hybridization the single-adapter tails of the immobilized targets hybridize to type C primers on the flow cell surface, which stabilizes a bridge structure. The 3' ends of immobilized targets and C primers are extended using DNA polymerase. After denaturation, two complementary, immobilized sequencing library fragments are formed that contain complete C and D priming sites and are compatible with solid-phase amplification. After the three steps of OS-Seq, immobilized targets are structurally identical to a standard paired-end Illumina library and are amplified and processed using Illumina's standard kits and protocols. The principles of this method may be employed on other sequencing platforms. (c) Shown is the coverage profile along the KRAS gene from the OS-Seq-366 assay. Base positions relative to the start of exon 1 are presented on the x-axis and KRAS exons are indicated. (d) Uniformity assessment of primer-probe yields within column and array-synthesized oligonucleotides. Uniformity of capture was compared between column-synthesized (blue, n=366) and array-synthesized (red, n=11,742) oligonucleotides. On the x-axis, oligonucleotides are sorted by sequence capture yields, on the y-axis is the normalized primer-probe yield. To calculate normalized yield, each oligonucleotide's yield was divided by the median yield from all oligonucleotides.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The term "sample" as used herein relates to a material or mixture of materials, typically, although not necessarily, in liquid form, containing one or more analytes of interest. The nucleic acid samples used herein may be complex in that they contain multiple different molecules that contain sequences. Fragmented genomic DNA and cDNA made from mRNA from a mammal (e.g., mouse or human) are types of complex samples. Complex samples may have more then $10^4$, $10^5$, $10^6$ or $10^7$ different nucleic acid molecules. A DNA target may originate from any source such as genomic DNA, cDNA (from RNA) or artificial DNA constructs. Any sample containing nucleic acid, e.g., genomic DNA made from tissue culture cells, a sample of tissue, or an FPET samples, may be employed herein.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively).

The term "nucleic acid sample," as used herein denotes a sample containing nucleic acids.

The term "target polynucleotide," as use herein, refers to a polynucleotide of interest under study. In certain embodiments, a target polynucleotide contains one or more sequences that are of interest and under study.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers. An oligonucleotide may be 10 to 20, 11 to 30, 31 to 40, 41 to 50, 51-60, 61 to 70, 71 to 80, 80 to 100, 100 to 150 or 150 to 200 nucleotides in length, for example.

The term "hybridization" refers to the process by which a strand of nucleic acid joins with a complementary strand through base pairing as known in the art. A nucleic acid is considered to be "Selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42 C in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

The term "amplifying" as used herein refers to generating one or more copies of a target nucleic acid, using the target nucleic acid as a template.

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "$T_m$" refers to the melting temperature of an oligonucleotide duplex at which half of the duplexes remain hybridized and half of the duplexes dissociate into single strands. The $T_m$ of an oligonucleotide duplex may be experimentally determined or predicted using the following formula $T_m=81.5+16.6(\log_{10}[Na^+])+0.41$ (fraction G+C)$-(60/N)$, where N is the chain length and $[Na^+]$ is less than 1 M. See Sambrook and Russell (2001; Molecular Cloning: A Laboratory Manual, $3^{rd}$ ed., Cold Spring Harbor Press, Cold Spring Harbor N.Y., ch. 10). Other formulas for predicting $T_m$ of oligonucleotide duplexes exist and one formula may be more or less appropriate for a given condition or set of conditions.

The term "free in solution," as used here, describes a molecule, such as a polynucleotide, that is not bound or tethered to another molecule.

The term "denaturing," as used herein, refers to the separation of a nucleic acid duplex into two single strands.

The term "genomic sequence", as used herein, refers to a sequence that occurs in a genome. Because RNAs are transcribed from a genome, this term encompasses sequence that exist in the nuclear genome of an organism, as well as sequences that are present in a cDNA copy of an RNA (e.g., an mRNA) transcribed from such a genome.

The term "genomic fragment", as used herein, refers to a region of a genome, e.g., an animal or plant genome such as the genome of a human, monkey, rat, fish or insect or plant. A genomic fragment may or may not be adaptor ligated. A genomic fragment may be adaptor ligated (in which case it has an adaptor ligated to one or both ends of the fragment, to at least the 5' end of a molecule), or non-adaptor ligated.

In certain cases, an oligonucleotide used in the method described herein may be designed using a reference genomic region, i.e., a genomic region of known nucleotide sequence, e.g., a chromosomal region whose sequence is deposited at NCBI's Genbank database or other database, for example. Such an oligonucleotide may be employed in an assay that uses a sample containing a test genome, where the test genome contains a binding site for the oligonucleotide.

The term "ligating", as used herein, refers to the enzymatically catalyzed joining of the terminal nucleotide at the 5' end of a first DNA molecule to the terminal nucleotide at the 3' end of a second DNA molecule.

The term "adaptor" refers to double stranded as well as single stranded molecules.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

If two nucleic acids are "complementary", each base of one of the nucleic acids base pairs with corresponding nucleotides in the other nucleic acid. The term "complementary" and "perfectly complementary" are used synonymously herein.

A "primer binding site" refers to a site to which a primer hybridizes in an oligonucleotide or a complementary strand thereof.

The term "separating", as used herein, refers to physical separation of two elements (e.g., by size or affinity, etc.) as well as degradation of one element, leaving the other intact.

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "not spatially addressed", in the context of a substrate containing surface-bound populations of oligonucleotides that are not spatially addressed, refers to a substrate that contains a surface containing different oligonucleotide molecules that are in no particular order or position relative to one another, i.e., at random positions or randomly interspersed with one another. Such a substrate need not be planer and in certain cases may be in the form of a bead. Substrates that contain spatially or optically addressed populations of a single oligonucleotide (e.g., microarrays and encoded beads etc.) are excluded by this definition. A substrate comprising a first population of surface-bound oligonucleotides and a second population of surface-bound oligonucleotides, wherein the first and second populations of surface-bound oligonucleotides not spatially addressed, refers to a substrate containing at least two populations of different oligonucleotides that are randomly distributed across the substrate. A substrate may planar or in the form of beads, for example.

The term "adaptor-ligated", as used herein, refers to a nucleic acid that has been ligated to an adaptor. The adaptor can be ligated to a 5' end or a 3' end of a nucleic acid molecule.

The term "extending", as used herein, refers to the extension of a primer by the addition of nucleotides using a polymerase. If a primer that is annealed to a nucleic acid is extended, the nucleic acid acts as a template for extension reaction.

The term "bridge PCR" refers to a solid-phase polymerase chain reaction in which the primers that are extended in the reaction are tethered to a substrate by their 5' ends. During amplification, the amplicons form a bridge between the tethered primers. Bridge PCR (which may also be referred to as "cluster PCR") is used in Illumina's Solexa platform. Bridge PCR and Illumina's Solexa platform are generally described in a variety of publications, e.g., Gudmundsson et al (Nat. Genet. 2009 41:1122-6), Out et al (Hum. Mutat. 2009 30:1703-12) and Turner (Nat. Methods 2009 6:315-6), U.S. Pat. No. 7,115,400, and publication application publication nos. US20080160580 and US20080286795.

The term "barcode sequence", as used herein, refers to a unique sequence of nucleotides is used to identify and/or track the source of a polynucleotide in a reaction. A barcode sequence may be at the 5'-end or 3'-end of a oligonucleotide. Barcode sequences may vary widely in size and composition; the following references provide guidance for selecting sets of barcode sequences appropriate for particular embodiments: Brenner, U.S. Pat. No. 5,635,400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981, 179; and the like. In particular embodiments, a barcode sequence may have a length in range of from 4 to 36 nucleotides, or from 6 to 30 nucleotides, or from 8 to 20 nucleotides.

Other definitions of terms may appear throughout the specification.

DETAILED DESCRIPTION OF EXEMPLARY EMBODIMENTS

Certain features of the subject method are described with reference to FIG. 1, which illustrates an embodiment in which adaptors are ligated to a fragment prior to hybridization of the fragment to the substrate. In alternative embodiments, an adaptor may be added later in the protocol. The method generally comprises obtaining a substrate that contains at least two surface bound oligonucleotides of differing sequence that are spatially interspersed with one another. Such substrates are currently employed in Illumina's Solexa sequencing technology and are described in a variety of references, e.g., U.S. Pat. No. 7,115,400 and publication nos. US20080160580 and US20080286795, which are incorporated by reference for such disclosure. Some of the embodiments set forth below may describe the use of the method to isolate fragments of a genome. These embodiments may be readily adapted to other types of sequences, e.g., cDNA or synthetic DNA.

In certain embodiments, a first member of the first population of surface-bound oligonucleotides is hybridized to a selection oligonucleotide that contains a) a region that hybridizes with the first member and a region, a sequencing primer site and b) a region that contains a target genomic sequence. The amount of selection oligonucleotide used in this step may be optimized such that sufficient number of oligonucleotides of the first population remain unhybridized to the selection oligonucleotide and available to be used in the bridge PCR step that occurs later in the protocol. The first member of the first population of surface-bound oligonucleotides is extended to produce a duplex that contains support-bound selection primer that contains a sequence that is complementary to the target genomic sequence. The selection oligonucleotide is removed by denaturation to leave the extended support-bound selection primer. The extended support-bound selection primer is then hybridized with adapter-ligated genomic fragment (which may be made by fragmenting genomic DNA, chemically, physically or using an enzyme and then ligating adaptors to the ends of the resultant fragments) containing the target genomic sequence, sequence that flanks the target genomic sequence, and an adaptor sequence at the 5' end of one or both of the strands. The support-bound selection primer is extended to produce a product that contains a sequence that flanks the genomic sequence in the genome and the sequence of the adaptor of the adaptor-ligated genomic fragment.

In some embodiments, the adaptor of the adaptor-ligated genomic fragment may hybridize to the second population of surface-bound oligonucleotides. However, in certain cases, before amplification, second population of surface-bound oligonucleotides may be hybridized to a modifying oligonucleotide that contains a) a region that hybridizes with second member and a region that contain contains adaptor sequence. The amount of modifying oligonucleotide used in this step may be optimized such that sufficient number of product molecules hybridize. The second member of the second population of surface-bound oligonucleotides may be extended to produce a duplex that contains support-bound adapter primer that contains a sequence that is complementary to the adapter sequence. The modifying oligonucleotide is removed by denaturation to leave support-bound adapter primer. The product may be then amplified by bridge PCR.

Figure 1B:
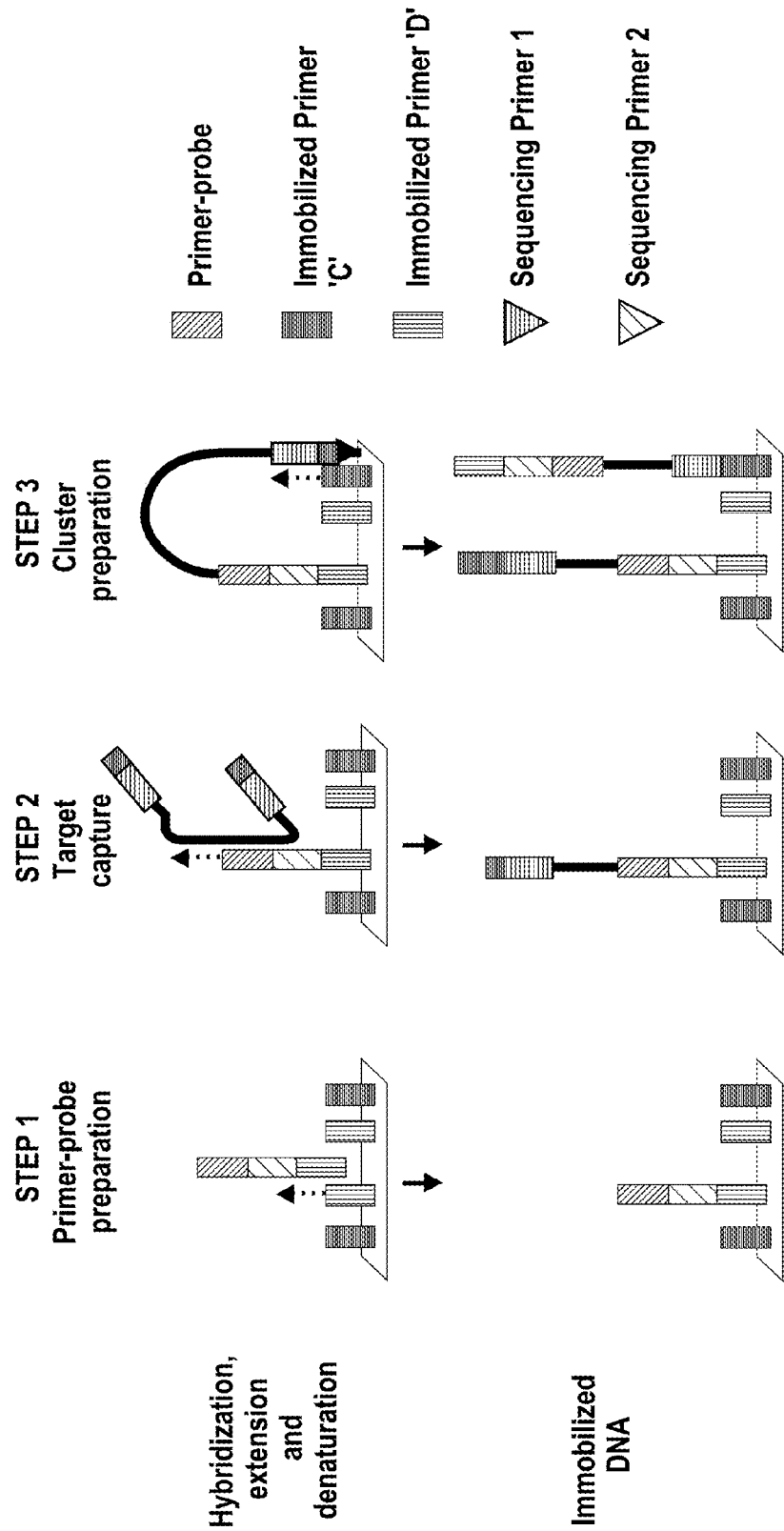
Figure 1D:
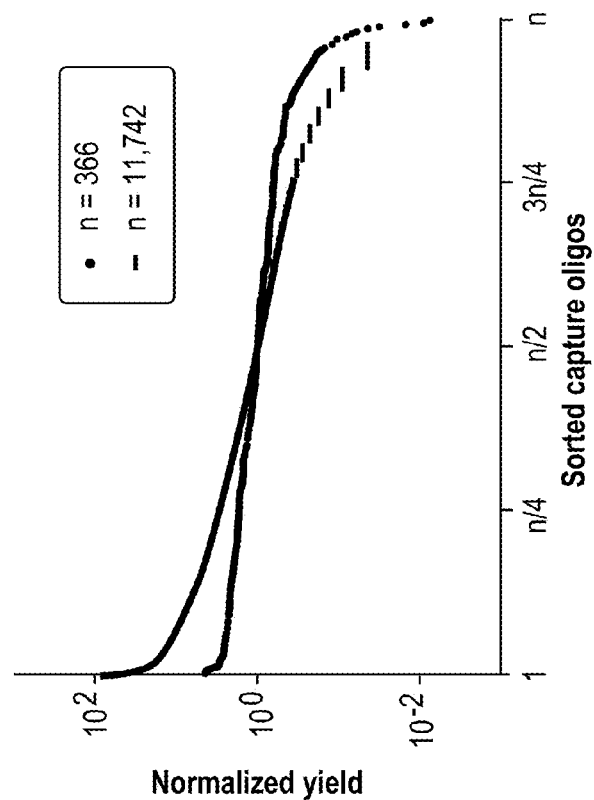

As illustrated in FIG. 1b, the product is amplified by a first unextended surface-bound oligonucleotides as well as a second surface-bound oligonucleotide to produce a PCR product. In certain cases, the genomic fragment is an adaptor-ligated genomic fragment comprising a 5' end adaptor. In these cases, members of the second population of the surface-bound oligonucleotides hybridize to the complement of the adaptor. In alternative embodiments, an adaptor may be ligated onto the extension product, thereby placing an adaptor that hybridizes to the second population of the surface-bound oligonucleotides onto the 3' end of the extension product. In other embodiments, the amplifying is done using: a) unextended members of the first population of surface-bound oligonucleotides; and b) support-bound primers that are made by: i. hybridizing members of the second population of surface-bound oligonucleotides to an oligonucleotide comprising a region that hybridizes with the members of the second population of surface-bound oligonucleotides and a region that is complementary to an adaptor; and ii. extending the members of the second population of surface-bound oligonucleotides to produce support-bound primers that hybridize to the 5' end of the extension product.

In some embodiments, the genomic fragment is an adaptor-ligated genomic fragment comprising a 5' end adaptor, wherein the extending produces an extension product that comprises, on its 3' end, a sequence that is complementary to the adaptor, and wherein members of the second population of the surface-bound oligonucleotides hybridize to the sequence that is complementary to the adaptor during the bridge PCR. In this embodiment, the 5' end adaptor comprises a binding site for a sequencing primer at the end that is ligated to the genomic fragment.

In other embodiments, the method comprises, between steps e) and f), ligating an adaptor onto the 3' end of the extension product, and wherein members of the second population of the surface-bound oligonucleotides hybridize to the adaptor during the bridge PCR. In these embodiments, the adaptor comprises a binding site for a sequencing primer at the end that is ligated to the genomic fragment.

In some embodiments, the second population of surface-bound oligonucleotides are made by: i. hybridizing members of an initial second population of surface-bound oligonucleotides to an oligonucleotide comprising a region that hybridizes with the members of the second population of surface-bound oligonucleotides and a region that is complementary to a sequence of the genomic fragment; and ii. extending the members of the initial second population of surface-bound oligonucleotides to produce the second population of surface-bound oligonucleotides.

In some embodiments, the second population of surface-bound oligonucleotides may be made by ligating an oligonucleotide comprising a region that is complementary to a sequence of said nucleic acid fragment to an initial second population of surface-bound oligonucleotides to produce said second population of surface-bound oligonucleotides. This ligation may be facilitated by a splint oligonucleotide that forms a bridge between the two oligonucleotides being ligated. In other words, a modifying oligonucleotide may be introduced by a ligation-based process in which a bridging oligonucleotide is used to guide the modification of the original solid support oligonucleotide to create the support-bound adapter primer. Similarly, the support-bound adapter primer can be created using a similar bridging oligonucleotide to create the primer extension necessary for the target modification.

In some cases the selection oligonucleotide comprises a binding site for a sequencing primer between said a region that hybridizes with said first member and said region that contains said genomic sequence.

In some embodiments, the method may further comprises sequencing a first strand of the PCR product to obtain at least part of the nucleotide sequence of the sequence that flanks the genomic sequence. This method may further comprise sequencing the second strand of the PCR product to obtain at least part of the nucleotide sequence of the sequence that flanks the genomic sequence.

In particular embodiments, the method may comprise fragmenting a mammalian genome to produce a fragmented genome, optionally adding adaptors to the fragmented genome, and applying the fragmented genome to the substrate. The fragmenting is done physically, chemically or using a restriction enzyme. The fragmenting is done by sonication or shearing, for example.

In particular cases, the hybridizing may be done by preparing a plurality of fragmented genomes from a plurality of different individuals, pooling the plurality of fragmented genomes to produce a pool, applying the pool of fragmented genomes to the substrate, and obtaining PCR products that comprise a sequence that flanks the genomic sequence in the different individuals. These embodiments may further comprising sequencing at least the first strand of the PCR products to obtain at least part of the nucleotide sequence of the sequence that flanks the genomic sequence in the different individuals. In particular cases, prior to pooling, different adaptors are ligated to the fragmented genomes from the different individuals, wherein the adaptor comprises a barcode sequence that allows the source of the adaptor-ligated genomic fragment to be identified after the PCR products are sequenced.

In some embodiments, the method comprises: adaptor-ligating fragmented genomic DNA from a first subject using a first adaptor that comprises a first barcode sequence to produce a first product; adaptor-ligating fragmented genomic DNA from a second subject using a second adaptor that comprises a second barcode sequence to produce a second product; combining the first and second products to produce a mixed template; and performing the method of claim 1 using the mixed template to provide first and second PCR product each containing the barcode sequence. The mixed template in some cases may comprise fragmented genomic DNA from at least 1,000 subjects.

In some embodiments, the method may involve i. ligating the genomic fragments to an adaptor that contains a site for a sequencing primer and a nucleotide sequence that is the same as the second surface bound oligonucleotides, ii. hybridizing the adaptor-ligated genomic fragments to a first member of the first population of surface-bound oligonucleotides, iii. extending the first member of the first population of surface-bound oligonucleotides to which the adaptor ligated fragment is hybridized; and iv. hybridizing the adaptor-containing end of the extension product to a second support bound polynucleotide, thereby producing a bridge and facilitating bridge PCR.

Also provided is a system. In certain cases the system may comprises: a) a substrate comprising a first population of surface-bound oligonucleotides and a second population of surface-bound oligonucleotides, wherein the first and second populations of surface-bound oligonucleotides not spatially addressed on the substrate; b) a selection oligonucleotide that contains a region that hybridizes with a first member of the first population and a region that contains a genomic sequence; c) an adaptor; and e) instructions for performing the method of claim 1. The PCR product may be sequenced, e.g., using Illumina's Solexa platform, or another solid-phase sequencing method, to obtain at least part of the nucleotide sequence of the sequence that flanks the targets genomic sequence.

In particular embodiments, the method may employ barcode sequences that allow the source of the sequence that flanks the target genomic sequence. In these embodiments, the adaptor of the adaptor-ligated genomic fragment may contain a barcode sequence that allows the source of the adaptor-ligated genomic fragment to be identified after PCR product is sequenced. In particular embodiments, this method comprises adaptor-ligating fragmented genomic DNA from a first subject (which subject may be included in a pool of first subjects) using a first adaptor that comprises a first barcode sequence to produce a first product; adaptor-ligating fragmented genomic DNA from a second subject (which subject may be included in a pool of second subjects) using a second adaptor that comprises a second barcode sequence to produce a second product; combining the first and second products to produce a mixed template; and performing the above-described method using the mixed template to provide first and second PCR products each containing the barcode sequence. In the above-method, the adaptors used have a portion that has the same sequence and that hybridizes to a surface-bound oligonucleotide, and a portion that has a different nucleotide sequence that contains the barcode sequence.

A second method of amplifying a selected sequence is provided. The principle of this method is similar to that of the method described above, except that a) the genomic fragment that is hybridized to the support-bound selection primer is not adaptor ligated; and b) adaptors are after the support-bound selection primer is extended. Adaptor ligation, the product may be employed in a bridge PCR reaction, as discussed above. As in the alternative embodiment described above, the amplifying is done using: a) unextended members of the first population of surface-bound oligonucleotides; and b) support-bound primers that are made by: i. hybridizing members of the second population of surface-bound oligonucleotides to an oligonucleotide comprising a region that hybridizes with the members of the second population of surface-bound oligonucleotides and a region that is complementary to the sequence of the adaptor; and ii. extending the members of the second population of surface-bound oligonucleotides to produce the support-bound primers. As with the method described above, the PCR product may be sequenced to obtain at least part of the nucleotide sequence of the sequence that flanks the genomic sequence.

In an alternative embodiment, the genomic fragments may be ligated to an adaptor that not only contains a sequencing primer binding site, but also a sequence that is the same as second population of surface-bound oligonucleotides. As shown, when the extended first population of surface-bound oligonucleotides (which is usually done at high temperature, i.e., at least 90° C.) are hybridized to the adaptor-ligated fragments and extended, the extension product contains a sequence that hybridizes to the second population of surface-bound oligonucleotides (which is usually done at a lower temperature, e.g., lower than 60° C., e.g., lower than 55° C.), thereby facilitating amplification of the genomic fragments using the first and second surface bound oligonucleotides. This method is illustrated in FIG. 14.

In particular embodiments, the oligonucleotides of the first population are present at a molar excess of at least 5×, 10×, 20×, 50×, or 100×, 500×, 1,000×, 2000×, 10,000×, 50,000× relative to the amount of selection oligonucleotide applied to the substrate. In one embodiment, the molar excess may be in the rage of a 5× to 50,000× molar excess, e.g., a 100× to 5,000× molar excess.

In certain embodiments, a substrate may be contacted with plurality of different selection oligonucleotides, each comprising a region that hybridizes with members of the first population of surface-bound oligonucleotides (which region has the same nucleotide sequence in the different selection oligonucleotides) and a region that contains a genomic sequence. The genomic sequence of each of the selection oligonucleotides is different, thereby allowing several genomic regions to be captured, amplified and sequenced on the substrate.

Kits

Also provided by the present disclosure are kits for practicing the subject method as described above. In certain embodiments, a subject kit may contain a) a substrate comprising a first population of surface-bound oligonucleotides and a second population of surface-bound oligonucleotides, wherein the first and second populations of surface-bound oligonucleotides not spatially addressed on the substrate and b) a selection oligonucleotide that contains a region that hybridizes with a first member of the first population and a region that contains a genomic sequence. The kit may also contains other reagents described above and below that may be employed in the method, e.g., adaptors, ligase, hybridization buffers, etc.

In addition to above-mentioned components, the subject kit typically further includes instructions for using the components of the kit to practice the subject method. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate. Other required components will include related computer programs and/or computer scripts to implement the a modification to prior programs already installed on a sequencer.

In addition to the instructions, the kits may also include one or more control analyte mixtures, e.g., two or more control analytes for use in testing the kit.

In order to further illustrate the present invention, the following specific examples are given with the understanding that they are being offered to illustrate the present invention and should not be construed in any way as limiting its scope.

The disclosure of U.S. provisional patent application Ser. No. 61/386,390, filed on Sep. 24, 2010, and 61/485,062 filed on May 11, 2011, including all figures, examples, detailed description, and oligonucleotide sequences, are incorporated herein in their entirety.

EXAMPLES

Presented below is a new approach to perform targeted DNA sequencing. The method is based on modifying a generic primer lawn (i.e. a lawn containing at least two primers that are randomly distributed) on a solid phase support to serve as a target DNA capture device, enabling direct sequencing of the captured DNA and without significant manipulation of the sample. The method enables seamless integration of target DNA capture and sequencing experiments with a related fluidics platform. This approach uses a universal primer lawn on a solid-phase support to serve as a DNA capture substrate while maintaining its sequencing potential. The method can use non-processed, natural DNA as a template for sequencing. Sequencing using this method is not necessarily dependent on laboratory facilities. Moreover, many of the biases introduced during sample processing are avoided and substantially smaller samples can be analyzed in lesser time and with reduced cost relative to other methods. The method can be used to analyze single and double stranded templates. The ability to analyze single-strand DNA templates can be important for some sequencing applications that use formalin-fixed paraffin-embedded samples from pathological archives. Similarly, by allowing single-strand DNA template sequencing, the method does not require complicated nucleic acid extraction steps and expensive fragmentation instrumentation that are designed to preserve the double-strand formation of the DNA. Rather, the sample may be prepared by lysis and heat fragmentation, which is inexpensive and effective. The straightforward capture sequencing assay is not restricted to human genomic DNA but other nucleic acid substrates, such as bacterial and viral DNA and RNA can be analyzed. Transcriptomes, noncoding and miRNAs can also be captured and sequenced. In addition nucleotide sequence capture and sequencing, other genetic and epigenetic properties can be studied, such as DNA methylation, large genomic rearrangements, and gene expression. The method may also be employed to select synthetic DNA from a population.

Generally, sequencing has been regarded as a process in which the DNA sample is structurally modified to facilitate the analysis on a sequencing system. The method described below modifies the sequencing system and therefore there is no need to modify and extensively prepare the sample. By functionalizing a generic primer lawn by using a synthetic DNA oligonucleotide library of target genes of non-processed samples may be directly assayed. To reduce non-specific capture, specific DNA components that provide sequences that are employed in the formation of the bridge-structure are brought-in sequentially, and the primer lawn is itself modified. Sequencing library preparation for all types of sequencers rely on adding specific double-strand adaptor sequences to the DNA template. Since the capture oligonucleotides served as adaptors immobilized on a solid support, the library preparation for the assay only required an addition of a single adaptor. This substantially shortens the sample processing and does not require clonal amplification nor gel electrophoresis based size separation. In certain cases a second adapter may be added to the captured template on a solid support. Certain embodiments of the method allow for the use of raw DNA as a sequencing template.

Several current methods for performing high throughput re-sequencing involve capturing the target DNA and sequencing as separate methods. This can in certain case lead to multiple problems including i) significant labor and time intensive manipulations of DNA material, ii) errors secondary to complex experimental protocols, iii) bias created by the selection and molecular amplification process and iv) requirements for large quantities of starting material. The method described below is believed to eliminate the source of many of these problems since it involves little or no up-front sample manipulation and is totally automatable and highly scalable.

As a proof-of-concept, all exons of 10 cancer genes in the human genome were sequenced to show that the assay is reproducible and can be used to capture and sequence specific regions of the genome. This assay technology was demonstrated with an Illumina Genome Analyzer but note that this approach is broadly applicable to any sequencer that uses a solid-phase support.

The methods described below, some of the principles of which are illustrated in FIG. 1, can be used to effectively capture any target DNA sequence and allows direct sequencing of the captured genomic fragments. Genomic DNA sample can be prepared for sequencing by a simple heat fragmentation step and the entire assay can be fully automated and performed on the solid support. The capture and subsequent reactions can be mediated by a fluidics system.

An additional embodiment provides a method that allows the preparation of DNA fragments for sequencing on the solid support by using fragmented DNA as a template and adding sequencing adapters to the captured DNA fragments using a fluidics system. As a proof-of concept an Illumina next-generation DNA sequencer was used to develop these approaches. The results from an integrated capture and sequencing preparation reaction using primer lawn modification and 366 target sites in the human genome are presented. With the exception of 25-minute heat fragmentation, all steps can be done on the solid-phase support of the Illumina flow cell.

The data described below demonstrates the robustness of the assay and applicability of a universal primer lawn and a fluidics system as a capture substrate. Unique parameters of the modification of primer lawns have been identified, which enable the method to work robustly. In addition to complex eukaryotic genomes, the method can be applied to capture microbial and other organisms' genomes, viral DNA and RNA, transcriptomes of different sources as well as synthetic DNA. Furthermore, the concept of "programming" a native primer lawn immobilized on a solid support of a fluidics system and executing specific applications is being introduced and validated.

Materials and Methods

Genomic DNA Samples.

Genomic DNA for NA18507 was obtained from the Coriell Institute. Fresh frozen tissue samples were obtained from a colorectal cancer patient. Patient material was obtained with informed consent from the Stanford Cancer Center and the study was approved by the institutional review board (IRB) at Stanford University School of Medicine. Frozen tissue sections were prepared, hematoxylin-eosin staining was performed and the tumor composition of each sample was determined via pathological examination. Samples representing tumor and normal tissues were dissected from areas where cellular composition was 90% tumor or purely normal, respectively. Genomic DNA was extracted using E.Z.N.A SQ DNA/RNA Protein Kit (Omega Bio-Tek, Norcross, Ga.). Standard protocols for DNA preparation, array hybridization and scanning were used to analyze samples using SNP 6.0 arrays (Affymetrix, Santa Clara, Calif.). Data analysis was performed using the Genotyping Console software and Birdseed V2 algorithm (Affymetrix). Thirteen additional microarray data sets were analyzed in concert with the studied samples in order to assess the quality of the SNP calls. SNP 6.0 array data was filtered using P-value threshold of 0.01.

Target Selection and in Silico OS-Seq Oligonucleotide Design.

Figure 3A:
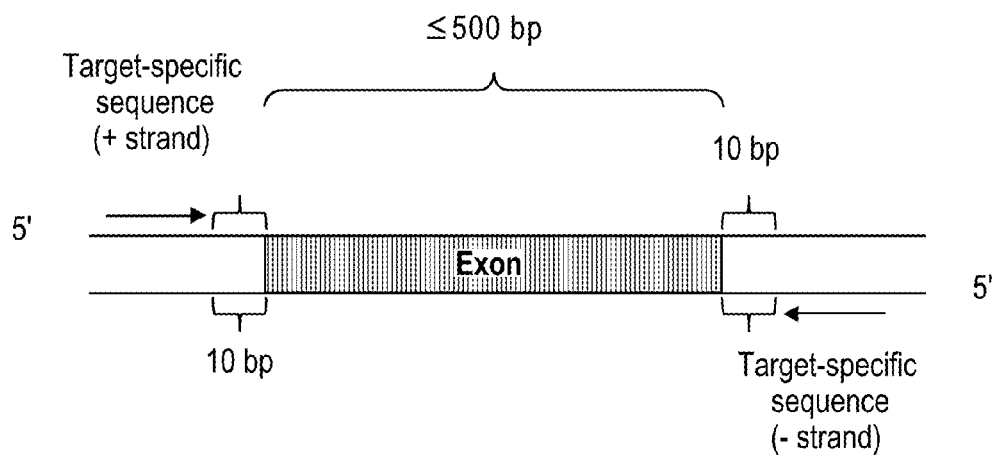
FIG. 3. Design strategies for OS-Seq. (a) Primer-probes were placed 10 bases from the exon or (b) tiled every 500 bases inside large exons.
Figure 3B:
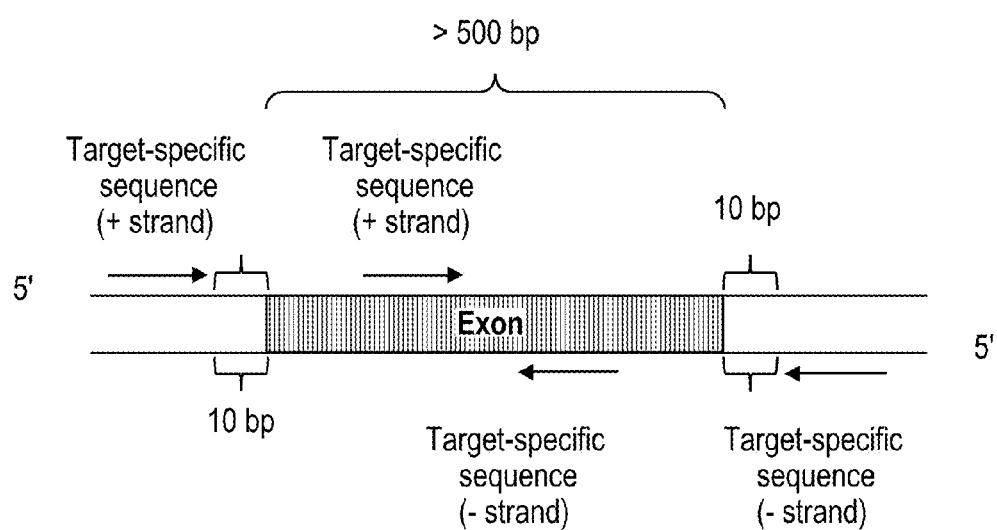

CCDS build release 20090902, human genome build NCBI 37-hg19 and dbSNP Build ID 131 were used as the polymorphism reference data set. For gene selection, the GeneRanker annotation database was used to choose 344 cancer genes prioritized by importance. In order to find target-specific sequences of oligonucleotides, the exon definitions for the candidate genes were taken from CCDS. For most targeted exons (less than 500 bp), the 40-mer target-specific sequences were 10 bases outside of the 5' end of the exon boundary (FIG. 3a). Both strands of the exons were targeted using individual primer-probes. OS-Seq-366 only covered the flanks of exons. In the OS-Seq-11k assay, exons larger than 500 bp were treated by tiling target-specific sequences until the entire exonic region was covered (FIG. 3b). To improve the on-target specificity of OS-Seq-11k, we used Repbase to identify and eliminate oligonucleotide sequences that targeted highly repetitive sequences.

Oligonucleotide Synthesis.

Two strategies were applied for oligonucleotide synthesis. For OS-Seq-366, we designed 366 101-mer oligonucleotides (FIG. 5a) which were then column-synthesized (Stanford Genome Technology Center, Stanford, Calif.) (FIG. 4a). Oligonucleotides were quantified and pooled in equimolar concentration. For OS-Seq-11k, an in-situ microarray synthesis (LC Sciences, Houston) approach was used to synthesize the 11,742 precursor oligonucleotides (FIG. 5b). The sequences of target-specific oligonucleotides are in Table 2 below.

| SEQ ID NO | Oligo Name | Sequence<br>x = phosphorothioate bond<br>p = 5'-phosphate |
|---|---|---|
| 1 | Ad_top_FC_capture_A_tail | CGAGATCTACACTCTTTCCCTACACGACGCTCTTCCGATCxT |
| 2 | Ad_bot_FC_capture_A_tail | p-GATCGGAAGAGCGTCGTGTAGGGAAAGAGTGTAGATCTCG |
| 3 | Ad_top_FC_capture_TGCTAA_1 | CGAGATCTACACTCTTTCCCTACACGACGCTCTTCCGATCTTGCTAAxT |
| 4 | Ad_top_FC_capture_AGGTCA_2 | CGAGATCTACACTCTTTCCCTACACGACGCTCTTCCGATCTAGGTCAxT |
| 5 | Ad_top_FC_capture_GGATTA_3 | CGAGATCTACACTCTTTCCCTACACGACGCTCTTCCGATCTGGATTAxT |
| 6 | Ad_top_FC_capture_CGTTGA_4 | CGAGATCTACACTCTTTCCCTACACGACGCTCTTCCGATCTCGTTGAxT |
| 7 | Ad_top_FC_capture_ATGATC_5 | CGAGATCTACACTCTTTCCCTACACGACGCTCTTCCGATCTATGATCxT |
| 8 | Ad_top_FC_capture_CTTAAC_6 | CGAGATCTACACTCTTTCCCTACACGACGCTCTTCCGATCTCTTAACxT |

-continued

| SEQ ID NO | Oligo Name | Sequence<br>x = phosphorothioate bond<br>p = 5'-phosphate |
|---|---|---|
| 9 | Ad_top_FC_capture_TTCAGC_7 | CGAGATCTACACTCTTTCCCTACACGACGCTCTTCCGATCTTTCAGCxT |
| 10 | Ad_top_FC_capture_GTAACC_8 | CGAGATCTACACTCTTTCCCTACACGACGCTCTTCCGATCTGTAACCxT |
| 11 | Ad_top_FC_capture_CCAGGT_9 | CGAGATCTACACTCTTTCCCTACACGACGCTCTTCCGATCTCCAGGTxT |
| 12 | Ad_top_FC_capture_GCCGTT_10 | CGAGATCTACACTCTTTCCCTACACGACGCTCTTCCGATCTGCCGTTxT |
| 13 | Ad_top_FC_capture_ACTGCT_11 | CGAGATCTACACTCTTTCCCTACACGACGCTCTTCCGATCTACTGCTxT |
| 14 | Ad_top_FC_capture_TCGGAT_12 | CGAGATCTACACTCTTTCCCTACACGACGCTCTTCCGATCTTCGGATxT |
| 15 | Ad_top_FC_capture_GATCCG_13 | CGAGATCTACACTCTTTCCCTACACGACGCTCTTCCGATCTGATCCGxT |
| 16 | Ad_top_FC_capture_TAACGG_14 | CGAGATCTACACTCTTTCCCTACACGACGCTCTTCCGATCTTAACGGxT |
| 17 | Ad_top_FC_capture-CAGCAG_15 | CGAGATCTACACTCTTTCCCTACACGACGCTCTTCCGATCTCAGCAGxT |
| 18 | Ad_top_FC_capture_AACCTG_16 | CGAGATCTACACTCTTTCCCTACACGACGCTCTTCCGATCTAACCTGxT |
| 19 | Ad_bot_FC_capture_TGCTAA_1 | p-TTAGCAAGATCGGAAGAGCGTCGTGTAGGGAAAGAGTGTAGATCTCG |
| 20 | Ad_bot_FC_capture_AGGTCA_2 | p-TGACCTAGATCGGAAGAGCGTCGTGTAGGGAAAGAGTGTAGATCTCG |
| 21 | Ad_bot_FC_capture_GGATTA_3 | p-TAATCCAGATCGGAAGAGCGTCGTGTAGGGAAAGAGTGTAGATCTCG |
| 22 | Ad_bot-FC_capture_CGTTGA_4 | p-TCAACGAGATCGGAAGAGCGTCGTGTAGGGAAAGAGTGTAGATCTCG |
| 23 | Ad_bot_FC_capture_ATGATC_5 | p-GATCATAGATCGGAAGAGCGTCGTGTAGGGAAAGAGTGTAGATCTCG |
| 24 | Ad_bot_FC_capture_CTTAAC_6 | p-GTTAAGAGATCGGAAGAGCGTCGTGTAGGGAAAGAGTGTAGATCTCG |
| 25 | Ad_bot_FC_capture_TTCAGC_7 | p-GCTGAAAGATCGGAAGAGCGTCGTGTAGGGAAAGAGTGTAGATCTCG |
| 26 | Ad_bot_FC_capture_GTAACC_8 | p-GGTTACAGATCGGAAGAGCGTCGTGTAGGGAAAGAGTGTAGATCTCG |
| 27 | Ad_bot_FC_capture_CCAGGT_9 | p-ACCTGGAGATCGGAAGAGCGTCGTGTAGGGAAAGAGTGTAGATCTCG |
| 28 | Ad_bot_FC_capture_GCCGTT_10 | p-AACGGCAGATCGGAAGAGCGTCGTGTAGGGAAAGAGTGTAGATCTCG |
| 29 | Ad_bot_FC_capture_ACTGCT_11 | p-AGCAGTAGATCGGAAGAGCGTCGTGTAGGGAAAGAGTGTAGATCTCG |
| 30 | Ad_bot_FC_capture_TCGGAT_12 | p-ATCCGAAGATCGGAAGAGCGTCGTGTAGGGAAAGAGTGTAGATCTCG |
| 31 | Ad_bot_FC_capture_GATCCG_13 | p-CGGATCAGATCGGAAGAGCGTCGTGTAGGGAAAGAGTGTAGATCTCG |
| 32 | Ad_bot_FC_capture_TAACGG_14 | p-CCGTTAAGATCGGAAGAGCGTCGTGTAGGGAAAGAGTGTAGATCTCG |
| 33 | Ad_bot_FC_capture_CAGCAG_15 | p-CTGCTGAGATCGGAAGAGCGTCGTGTAGGGAAAGAGTGTAGATCTCG |
| 34 | Ad_bot_FC_capture_AACCTG_16 | p-CAGGTTAGATCGGAAGAGCGTCGTGTAGGGAAAGAGTGTAGATCTCG |
| 35 | Microarray_oligo_amp_primer_1_U | GCTGACCTTAAACCTAACGCGAGGGCGGCAGTTGGGATTTCGTGACCTATGCACCAGACGU |
| 36 | Microarray_oligo_amp_primer_2 | CAAGCAGAAGACGGCATACGAGATCGGTCTCGGCATTCCTGCTGAACCGCTCTTCCGATCT |

Amplification of Microarray-Synthesized Oligonucleotides.

Three 25 µl subpools of precursor 80-mer oligonucleotides were used (587, 638 and 415 nM) (FIG. 5b). A PCR approach was employed to amplify the precursor, low-concentration oligonucleotides (FIG. 4b). The array-synthesized oligonucleotide subpools were diluted to 10 fM/oligo and used as a template for PCR amplification. PCR was performed using Taq DNA polymerase (NEB), and dNTPs (1 mM dATP, 1 mM dCTP, 1 mM cGTP, 500 nM dTTP and 500 nM dUTP) in standard reaction conditions. After denaturation in 95° C. for 30 s., 20 amplification cycles (95° C., 30 s.; 55° C., 30 s.; 68° C., 30 s.) were performed. Amplification Primer 1 contained uracil at the 3' end, while Amplification Primer 2 incorporated additional functional sequences (FIG. 5b). Amplified oligonucleotides were purified to remove excess primer (Fermentas), then processed using 0.1 U/µl Uracil DNA-excision Mix (Epicentre, Madison, Wis.) in 37° C. for 45 min to detach the universal amplification primer site and cleave the mature 101-mer coding strands of the oligonucleotides. The oligonucleotides require the 5' ends to be functional and free in order to have accurate extension of the target-specific site during primer-probe immobilization. After heat shock inactivation of the enzymes (65° C., 10 min), the oligonucleotide preparations were purified (Fermentas). Finally, we quantified the three oligonucleotide subpools and created a single pool with equimolar concentration of each subpool.

Preparation of OS-Seq Primer-Probes by Modification of the Flow Cell Primer Lawn.

In the Illumina Genome Analyzer IIx (Illumina, San Diego) system, the solid phase support (i.e. the flow cell) has two primers ('C' and 'D'), which are randomly immobilized on a polyacrylamide layer at extremely high density. For OS-Seq experiments, a subset of the 'D' primers was specifically modified using the Illumina Cluster station. Prior to the NGS primer modification, 133 nM oligonucleotide pools were heat denatured at 95° C. for 5 min. We used heat shock (95° C. for 5 min) to free the coding strand of the OS-Seq oligucleotides. Additional strand purification was not required as the second strand is inactive on the flow cell and is washed away after hybridization. Denatured oligonucleotides were diluted with 4× Hybridization buffer (20×SSC, 0.2% Tween-20). The resulting 100 nM oligonucleotides were used in the flow cell modification experiments. 30 µl of oligonucleotide mixture was dispensed into each lane of the flow cell. During a temperature ramp (from 96° C. to 40° C. in 18 minutes) oligonucleotides annealed specifically to the immobilized primer 'D'. Then, DNA polymerase was used to extend the 'D' primer with the annealed oligonucleotide as a template. After extension, the original oligonucleotide template was denatured from the extended 'D' primer and washed from the solid phase support. Standard Illumina v4 reagents were used for extension, wash and denaturation steps. The modification of primer 'D' caused immobilization of the primer-probes.

Sequencing Library Preparation.

Figure 2:
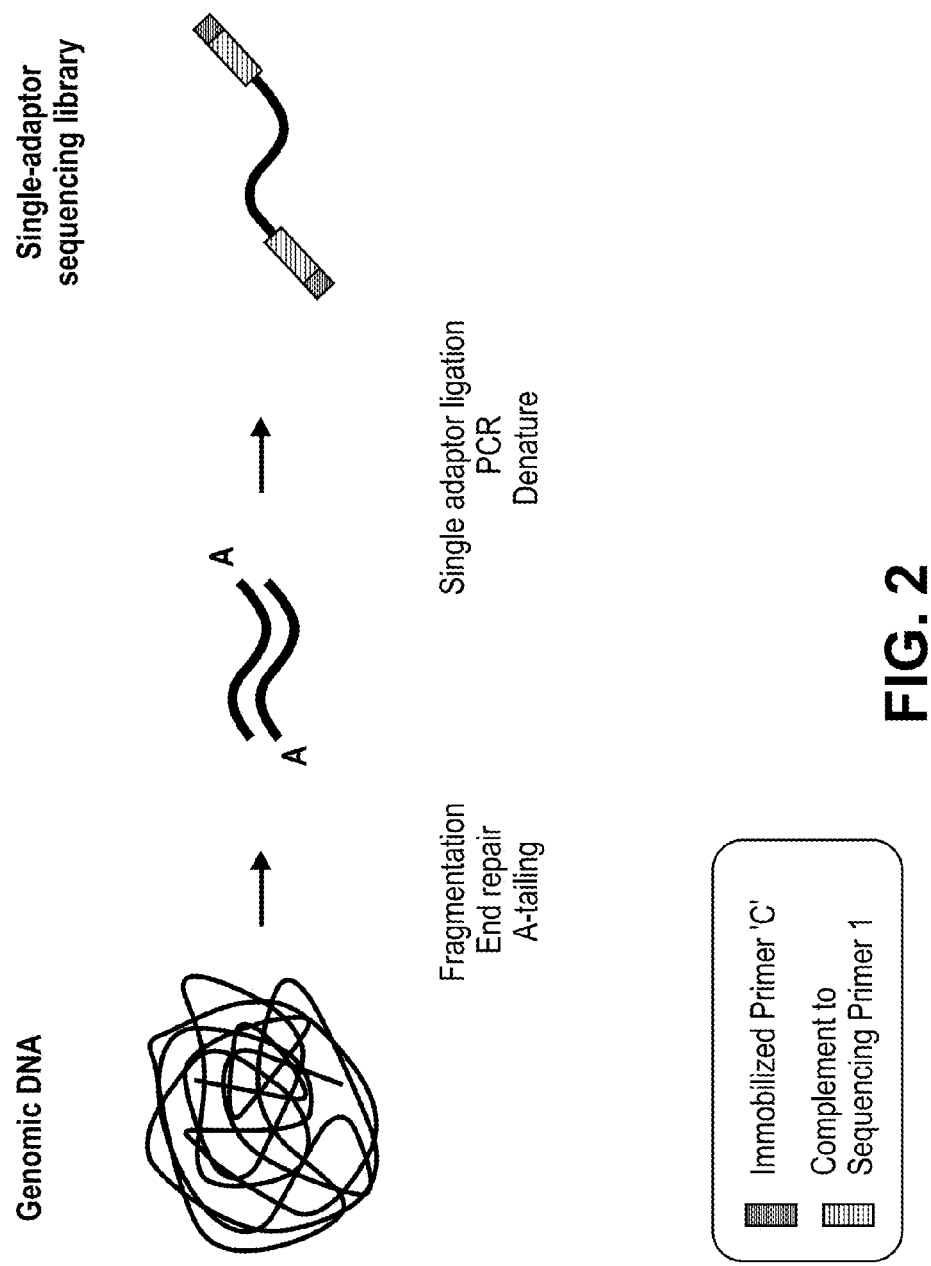
FIG. 2: Sequencing library preparation for OS-Seq. A general scheme of genomic DNA fragmentation, end repair, A-tailing, Adaptor ligation and PCR was used in the preparation of OS-Seq libraries.

We outline the general scheme of genomic DNA fragmentation, end repair, A-tailing, adapter ligation and PCR used in the preparation of the OS-Seq sequencing library in FIG. 2. We used 1 µg of genomic DNA from NA18507 and a flash frozen colorectal cancer sample as starting material. Genomic DNA was fragmented using Covaris E210R (Covaris, Woburn, Mass.) to obtain a mean fragment size of 500 bp (duty cycle 5%, intensity 3, 200 cycles per burst and 80 seconds). The randomly fragmented DNA was end-repaired using 0.25 U of Klenow large fragment (New England Biolabs, Ipswich, Mass.), 7.5 U of T4 DNA polymerase (NEB), 400 µM of each dNTP (NEB), 25 U of T4 Polynucleotide kinase (NEB) and T4 DNA ligase buffer with ATP (NEB) in 50 µl reaction volume at room temperature for 45 minutes. After end repair, adenines were added to the 3' ends of the template DNA using 3.2 U of Taq DNA polymerase (NEB), 100 µM dATP (Invitrogen) and Taq buffer with 1.5 mM MgCl2 in 80 ul reaction in 72° C. for 15 min. Before adapter ligation, reactions were purified using PCR purification kit (Fermentas).

An indexing system for OS-Seq was developed. The sequencing library adapters contain an optional 6-base indexing sequence, a sequencing primer 1 site and a 12-mer sequence for primer 'C' hybridization (Table 2 above, FIG. 5c). Designed sixteen indexing adapters were designed. Adapter oligonucleotides were synthesized at the Stanford Genome Technology Center. Prior to ligation, adapter oligonucleotides were annealed during temperature ramp down. For the targeted resequencing of NA18507, we used both a singleplex adapter as well as a multiplex adapter with 'AACCTG' tag. For the indexing of the matched normal tumor sample, we used a 'TGCTAA' barcode for the normal tissue while the tumor sample was tagged with 'AGGTCA'. Double-strand DNA adapters with T-overhang were ligated to the A-tailed templates using 2,000 U of T4 DNA ligase (NEB) and T4 DNA ligase buffer in room temperature for 1 hour. After adaptor ligation, reactions were purified using PCR purification kit (Fermentas) and libraries were amplified using PCR. 50 ul reactions of 1 U of Phusion Hot Start DNA polymerase (Finnzymes, Finland), 1 µM library amplification primer (Supplemental Table 1), Phusion HF buffer and 200 µM of each dNTP (NEB) were prepared. Reactions were denatured in 98° C. for 30 s. After that, 22 PCR cycles were performed (98° C. for 10 s, 65° C. for 30 s and 72° C. for 30 s) followed by 72° C. for 7 min and 4° C. Thereafter, PCR reactions were purified using PCR purification kit (Fermentas) and quantified. Multiplexed libraries were pooled in equal concentrations.

Capture of Targets Using Primer-Probes.

Targets were captured on the flow cell using OS-Seq primer-probes (FIG. 1b and oligonucleotide sequences below). We injected 30 ul of the genomic sequencing libraries (30-42 ng/ul) into the flow cell. Target DNA was hybridized to the primer-probes by incubating the sequencing libraries in the flow cell at 65° C. for 20 hours. During genomic DNA library hybridization and subsequent extension, the flow cell was kept at a constant 65° C. An Illumina Cluster Station was used to carry out the primer-probe hybridization and extension steps. Prior to hybridization to primer-probes, 22.5 µl of sequencing libraries (40-56.6 ng/µl) was denatured at 95° C. for 5 min. After heat shock, the genomic DNA libraries were diluted to a total volume of 30 µl using 4× Hybridization buffer. The final DNA concentrations of sequencing libraries ranged from 30 to 41.7 ng/µl. Due to the high concentration of the sequencing libraries, the hybridization volume was kept at minimum. Therefore, a custom Cluster Station program was developed to allow reproducible low-volume hybridization. The following extension, wash and denaturation steps were performed using Illumina v4 reagents.

Flow Cell Processing and Sequencing.

After capture of the targets, the temperature of the flow cell was lowered to 40° C. for 30 min to allow the 12 bases in the 3' end of the captured genomic DNA library fragments to hybridize to primer 'C' (FIG. 1b and oligonucleotide sequences below). In the bridge formation, the library fragment and primer 'C' were extended using DNA polymerase to finalize and replicate the captured DNA fragment. Afterwards, bridge-PCR was carried out to generate the clonally amplified sequencing clusters. Samples were sequenced using 40 by 40 (OS-Seq-366) or 60 by 60 (OS-Seq-11k) paired-end cycles on an Illumina Genome Analyzer IIx using regular version 4 sequencing reagents and recipes (Illumina). Image analysis and base calling were performed using the SCS 2.8 and RTA 2.8 software (Illumina).

Sequence Analysis and Variant Detection.

Sequence reads were aligned to the human genome version human genome build NCBI 37-hg19 using Burrows-Wheeler Aligner (BWA)[19]. After alignment, on-target reads (Read 1) were defined as being within 1 kb of the 5' end of the primer-probe. Off-target reads were defined as aligning outside 1 kb of the 5' end of the primer-probe or mapping on a different chromosome from the location of the associated primer-probe. For the de-multiplexing of indexed lanes, we used a perl script to generate an index of the 7-base tags using the base-call files. This index file and another perl script were used to de-multiplex either the combined base-call file (so that separate fastq files can be generated for further processing) or the aligned file.

To eliminate any synthetic primer-probe sequences for variant calling, insert size filtering on the mate pairs was applied. The insert size was determined by comparing alignment of paired sequence reads. For variant calling, extracted sequences were required to have an insert size greater than [40+the length of Read 1]. After insert size filtering, variant calling was performed using SAMtools and BCFtools. A sequence pileup was performed against the human genome (hg19) using SAMtools mpileup with a mapping quality threshold of 50. BCFtools view was used to genotype base positions and data was filtered using vcfutils.pl, a variant filter perl script provided in the SAMtools package. The vcfutils varFilter conditions were: i) coverage of 10 or greater, ii) removal of the strand bias filter (since OS-Seq is a strand-specific capture method), iii) forcing the script to output both reference and non-reference positions. Reference and non-reference calls were used for comparisons with the Affymetrix SNP 6.0 array data. Genotyped positions were filtered to have a Phred-like quality score above 50. We used BEDtools intersectBed to define target regions for each primer-probe and combinations where probes overlap in their targets.

Variant Comparison.

For quality assessment of extracted variants, variant calls of the NA18507 data were compared to calls from variants identified from a complete genome sequence analysis[3] and Hapmap genotyping data (www.hapmap.org). Comparisons of OS-Seq data and Affymetrix SNP 6.0 array data were made using perl scripts. dbSNP131 was used for SNP annotation.

```
Further Oligonucleotide sequences
0) Oligonucleotides
OS-Seq oligonucleotide:
                                                    (SEQ ID NO: 37)
5'-
NNNNNNNNNNNNNNNNNNNNNNNNNNNNNNNNNNNNNNNNAGATCGGAAGAGCGGTTCAGCAGG
AATGCCGAGACCGATCTCGTATGCCGTCTTCTGCTTG- 3'
(Generic capture oligonucleotide, N = unique 40-mer sequence;

Ad_top_FC_capture_A_tail:
                                                    (SEQ ID NO: 38)
5'- CGAGATCTACACTCTTTCCCTACACGACGCTCTTCCGATCT -3'

Ad_bot_FC_capture_A_tail:
                                                    (SEQ ID NO: 39)
5'- GATCGGAAGAGCGTCGTGTAGGGAAAGAGTGTAGATCTCG -3'

Flow cell primer 'C':
                                                    (SEQ ID NO: 40)
5'- PS-TTTTTTTTTTAATGATACGGCGACCACCGAGAUCTACAC -3'
(U = 2-deoxyuridine)

Flow cell primer 'D':
                                                    (SEQ ID NO: 41)
5'- PS-TTTTTTTTTTCAAGCAGAAGACGGCATACGAGoxoAT -3',
(Goxo = 8-oxoguanine)

Sequencing primer 1:
                                                    (SEQ ID NO: 42)
5'- ACACTCTTTCCCTACACGACGCTCTTCCGATCT -3'

Sequencing primer 2:
                                                    (SEQ ID NO: 43)
5'- CGGTCTCGGCATTCCTGCTGAACCGCTCTTCCGATCT -3'

1) Flow cell modification
Anneal
                                                    (SEQ ID NO: 44)
3'-
GTTCGTCTTCTGCCGTATGCTCTAGCCAGAGCCGTAAGGACGACTTGGCGAGAAGGCTAGANNNNN
NNNNNNNNNNNNNNNNNNNNNNNNNNNNNNNNNNNNN -5'
(OS-Seq oligonucleotide)

(SEQ ID NO: 45)
FC- CAAGCAGAAGACGGCATACGAGAT -3'
(Flow cell primer 'D')

Extension
                                                    (SEQ ID NO: 46)
3'-
GTTCGTCTTCTGCCGTATGCTCTAGCCAGAGCCGTAAGGACGACTTGGCGAGAAGGCTAGANNNNN
NNNNNNNNNNNNNNNNNNNNNNNNNNNNNNNNNNNNN -5'
(OS-Seq oligonucleotide)

(SEQ ID NO: 47)
FC-
CAAGCAGAAGACGGCATACGAGATCGGTCTCGGCATTCCTGCTGAACCGCTCTTCCGATCTNNNNN
NNNNNNNNNNNNNNNNNNNNNNNNNNNNNNNNNNNNN -3' (primer-probe)

Denature
                                                    (SEQ ID NO: 48)
FC-
CAAGCAGAAGACGGCATACGAGATCGGTCTCGGCATTCCTGCTGAACCGCTCTTCCGATCTNNNNN
NNNNNNNNNNNNNNNNNNNNNNNNNNNNNNNNNNNNN -3' (primer-probe)
```

2) Library prep
Fragmentation, end repair
5'- NNNNNNNNNNNNNNNNNNNNNNNN -3' (genomic DNA)

3'- NNNNNNNNNNNNNNNNNNNNNNNN -5' (genomic DNA)

A-tailing
5'- NNNNNNNNNNNNNNNNNNNNNNNNA -3' (genomic DNA after A-tailing)

3'- ANNNNNNNNNNNNNNNNNNNNNNNN -5' (genomic DNA after A-tailing)

Adaptor ligation
OS-Seq dsAdapter
                                                         (SEQ ID NO: 49)
5'- GATCGGAAGAGCGTCGTGTAGGGAAAGAGTGTAGATCTCG -3'
(Ad_bot_FC_capture_A_tail)

(SEQ ID NO: 50)
3'- TCTAGCCTTCTCGCAGCACATCCCTTTCTCACATCTAGAGC -5'
(Ad_top_FC_capture_A_tail)

OS-Seq dsAd library (This is the structure of the OS-Seq-adaptor
library, N = random genomic DNA sequence defined by fragmentation)
                                                         (SEQ ID NO: 51)
5'-
CGAGATCTACACTCTTTCCCTACACGACGCTCTTCCGATCTNNNNNNNNNNNNNNNNNNNNNNNNAGA
TCGGAAGAGCGTCGTGTAGGGAAAGAGTGTAGATCTCG -3'

(SEQ ID NO: 52)
3'-
GCTCTAGATGTGAGAAAGGGATGTGCTGCGAGAAGGCTAGANNNNNNNNNNNNNNNNNNNNNNNNNTC
TAGCCTTCTCGCAGCACATCCCTTTCTCACATCTAGAGC -5'

Library PCR
OS-Seq adaptor library amplification (Ad_top_FC_capture_A_tail,
single primer PCR is used to amplify the adaptor library)
                                                         (SEQ ID NO: 53)
5'- CGAGATCTACACTCTTTCCCTACACGACGCTCTTCCGATCT -3'
(Ad_top_FC_capture_A_tail)

(SEQ ID NO: 54)
3'-
GCTCTAGATGTGAGAAAGGGATGTGCTGCGAGAAGGCTAGANNNNNNNNNNNNNNNNNNNNNNNNNTC
TAGCCTTCTCGCAGCACATCCCTTTCTCACATCTAGAGC -5'
(OS-Seq library fragment)

(SEQ ID NO: 55)
5'-
CGAGATCTACACTCTTTCCCTACACGACGCTCTTCCGATCTNNNNNNNNNNNNNNNNNNNNNNNNAGA
TCGGAAGAGCGTCGTGTAGGGAAAGAGTGTAGATCTCG -3'
(OS-Seq library fragment)

(SEQ ID NO: 56)
3'-TCTAGCCTTCTCGCAGCACATCCCTTTCTCACATCTAGAGC -5'
(Ad_top_FC_capture_A_tail)

(SEQ ID NO: 57)
5'-
CGAGATCTACACTCTTTCCCTACACGACGCTCTTCCGATCTNNNNNNNNNNNNNNNNNNNNNNNNAGA
TCGGAAGAGCGTCGTGTAGGGAAAGAGTGTAGATCTCG -3'
(OS-Seq library fragment, amplified)

(SEQ ID NO: 58)
3'-
GCTCTAGATGTGAGAAAGGGATGTGCTGCGAGAAGGCTAGANNNNNNNNNNNNNNNNNNNNNNNNNTC
TAGCCTTCTCGCAGCACATCCCTTTCTCACATCTAGAGC -5'
(OS-Seq library fragment, amplified)

3) Capture
Anneal
OS-Seq adaptor library annealing
(N = 40-mer specific capture site)
                                                         (SEQ ID NO: 59)
3'- GCTCTAGATGTGAGAAAGGGATGTGCTGCGAGAAGGCTAGAgenomicdna (SEQ ID NO: 60)
NNNNNNNNNNNNNNNNNNNNNNNNNNNNNNNNNNNNNNNNgenomicdnaTCTAGCCTTCTCGCAGC
ACATCCCTTTCTCACATCTAGAGC -5'
(OS-Seq library fragment, amplified)

-continued (SEQ ID NO: 61)
FC-
CAAGCAGAAGACGGCATACGAGATCGGTCTCGGCATTCCTGCTGAACCGCTCTTCCGATCTNNNNN
NNNNNNNNNNNNNNNNNNNNNNNNNNNNNNNNN -3' (primer-probe)

Extension
OS-Seq capture (SEQ ID NO: 62)
3'- GCTCTAGATGTGAGAAAGGGATGTGCTGCGAGAAGGCTAGAgenomicdna (SEQ ID NO: 63)
NNNNNNNNNNNNNNNNNNNNNNNNNNNNNNNNNNNNNNNgenomicdnaTCTAGCCTTCTCGCAGC
ACATCCCTTTCTCACATCTAGAGC -5'
(OS-Seq library fragment, amplified)

(SEQ ID NO: 64)
FC-
CAAGCAGAAGACGGCATACGAGATCGGTCTCGGCATTCCTGCTGAACCGCTCTTCCGATCTNNNNN
NNNNNNNNNNNNNNNNNNNNNNNNNNNNNNNNNgenomicdnaAGATCGGAAGAGCGTCGTGTAG
GGAAAGAGTGTAGATCTCG -3' (captured DNA)

Denature
OS-Seq library (SEQ ID NO: 65)
FC-
CAAGCAGAAGACGGCATACGAGATCGGTCTCGGCATTCCTGCTGAACCGCTCTTCCGATCTNNNNN
NNNNNNNNNNNNNNNNNNNNNNNNNNNNNNNNNgenomicdnaAGATCGGAAGAGCGTCGTGTAG
GGAAAGAGTGTAGATCTCG -3' (captured DNA)

4) Adapter finalizing
Hybridization in 40C
OS-Seq_Library (there is 12-mer homology between the OS-Seq
adaptor and Oligo-C)

(SEQ ID NO: 66)
FC-
CAAGCAGAAGACGGCATACGAGATCGGTCTCGGCATTCCTGCTGAACCGCTCTTCCGATCTNNNNN
NNNNNNNNNNNNNNNNNNNNNNNNNNNNNNNNNgenomicdnaAGATCGGAAGAGCGTCGTGTAG
GGAAAGAGTGTAGATCTCG -3' (captured DNA)

(SEQ ID NO: 67)
3'-
CACATCTAGAGCCACCAGCGGCATAGTAA - FC (Oligo'C')

Extend (SEQ ID NO: 68)
FC -
CAAGCAGAAGACGGCATACGAGATCGGTCTCGGCATTCCTGCTGAACCGCTCTTCCGATCTNNNNN
NNNNNNNNNNNNNNNNNNNNNNNNNNNNNNNNNgenomicdnaAGATCGGAAGAGCGTCGTGTAG
GGAAAGAGTGTAGATCTCGGTGGTCGCCGTATCATT -3' (finalized DNA)

(SEQ ID NO: 69)
3'-
GTTCGTCTTCTGCCGTATGCTCTAGCCAGAGCCGTAAGGACGACTTGGCGAGAAGGCTAGANNNNN
NNNNNNNNNNNNNNNNNNNNNNNNNNNNNNNNNgenomicdnaTCTAGCCTTCTCGCAGCACATCC
CTTTCTCACATCTAGAGCCACCAGCGGCATAGTAA - FC (finalized DNA)

Denature (SEQ ID NO: 70)
FC -
CAAGCAGAAGACGGCATACGAGATCGGTCTCGGCATTCCTGCTGAACCGCTCTTCCGATCTNNNNN
NNNNNNNNNNNNNNNNNNNNNNNNNNNNNNNNNgenomicdnaAGATCGGAAGAGCGTCGTGTAG
GGAAAGAGTGTAGATCTCGGTGGTCGCCGTATCATT -3' (finalized DNA)

(SEQ ID NO: 71)
3'-
GTTCGTCTTCTGCCGTATGCTCTAGCCAGAGCCGTAAGGACGACTTGGCGAGAAGGCTAGANNNNN
NNNNNNNNNNNNNNNNNNNNNNNNNNNNNNNNNgenomicdnaTCTAGCCTTCTCGCAGCACATCC
CTTTCTCACATCTAGAGCCACCAGCGGCATAGTAA - FC (finalized DNA)

5) Cluster generation
Anneal (SEQ ID NO: 72)
FC-
CAAGCAGAAGACGGCATACGAGATCGGTCTCGGCATTCCTGCTGAACCGCTCTTCCGATCTNNNNN
NNNNNNNNNNNNNNNNNNNNNNNNNNNNNNNNNgenomicdnaAGATCGGAAGAGCGTCGTGTAG
GGAAAGAGTGTAGATCTCGGTGGTCGCCGTATCATT -3' (finalized DNA)

(SEQ ID NO: 73)
3'-
CACATCTAGAGCCACCAGCGGCATAGTAA - FC
(Oligo'C')

```
                                                          (SEQ ID NO: 74)
FC - CAAGCAGAAGACGGCATACGAGAT -3'
(Oligo 'D')

(SEQ ID NO: 75)
3'-
GTTCGTCTTCTGCCGTATGCTCTAGCCAGAGCCGTAAGGACGACTTGGCGAGAAGGCTAGANNNNN
NNNNNNNNNNNNNNNNNNNNNNNNNNNNNNNNNNNNNNNNgenomicdnaTCTAGCCTTCTCGCAGCACATCC
CTTTCTCACATCTAGAGCCACCAGCGGCATAGTAA - FC (finalized DNA)

Extend
                                                          (SEQ ID NO: 76)
FC-
CAAGCAGAAGACGGCATACGAGATCGGTCTCGGCATTCCTGCTGAACCGCTCTTCCGATCTNNNNN
NNNNNNNNNNNNNNNNNNNNNNNNNNNNNNNNNNNNNNNNgenomicdnaAGATCGGAAGAGCGTCGTGTAG
GGAAAGAGTGTAGATCTCGGTGGTCGCCGTATCATT -3' (finalized DNA)

(SEQ ID NO: 77)
3'-
GTTCGTCTTCTGCCGTATGCTCTAGCCAGAGCCGTAAGGACGACTTGGCGAGAAGGCTAGANNNNN
NNNNNNNNNNNNNNNNNNNNNNNNNNNNNNNNNNNNNNNNgenomicdnaTCTAGCCTTCTCGCAGCACATCC
CTTTCTCACATCTAGAGCCACCAGCGGCATAGTAA - FC (finalized DNA)

Denature
                                                          (SEQ ID NO: 78)
FC-
CAAGCAGAAGACGGCATACGAGATCGGTCTCGGCATTCCTGCTGAACCGCTCTTCCGATCTNNNNN
NNNNNNNNNNNNNNNNNNNNNNNNNNNNNNNNNNNNNNNNgenomicdnaAGATCGGAAGAGCGTCGTGTAG
GGAAAGAGTGTAGATCTCGGTGGTCGCCGTATCATT -3' (Clustered DNA)

(SEQ ID NO: 79)
3'-
GTTCGTCTTCTGCCGTATGCTCTAGCCAGAGCCGTAAGGACGACTTGGCGAGAAGGCTAGANNNNN
NNNNNNNNNNNNNNNNNNNNNNNNNNNNNNNNNNNNNNNNgenomicdnaTCTAGCCTTCTCGCAGCACATCC
CTTTCTCACATCTAGAGCCACCAGCGGCATAGTAA - FC (Clustered DNA)

6) Sequencing
                                                          (SEQ ID NO: 80)
FC-
CAAGCAGAAGACGGCATACGAGATCGGTCTCGGCATTCCTGCTGAACCGCTCTTCCGATCTNNNNN
NNNNNNNNNNNNNNNNNNNNNNNNNNNNNNNNNNNNNNNNgenomicdnaAGATCGGAAGAGCGTCGTGTAG
GGAAAGAGTGTAGATCTCGGTGGTCGCCGTATCATT -3' (Clustered DNA)

(SEQ ID NO: 81)
3'- <- - - -
TCTAGCCTTCTCGCAGCACATCCCTTTCTCACA - 5' (Sequencing Primer 1)

(SEQ ID NO: 82)
5'- CGGTCTCGGCATTCCTGCTGAACCGCTCTTCCGATCT- - - ->
(Sequencing Primer 2)

(SEQ ID NO: 83)
3'-
GTTCGTCTTCTGCCGTATGCTCTAGCCAGAGCCGTAAGGACGACTTGGCGAGAAGGCTAGANNNNN
NNNNNNNNNNNNNNNNNNNNNNNNNNNNNNNNNNNNNNNNgenomicdnaTCTAGCCTTCTCGCAGCACATCC
CTTTCTCACATCTAGAGCCACCAGCGGCATAGTAA - FC (Clustered DNA)
```

Results

This section describes a new approach for targeted resequencing called Oligonucleotide-Selective Sequencing (OS-Seq) that solves many of the limitations seen in targeted resequencing approaches. Conceptually different than other methods, OS-Seq is an integrated approach in which both capture and sequencing of genomic targets are performed on the NGS solid phase support, such as the Illumina flow cell (FIG. 1a). For preparation of OS-Seq, a single-adapter sequencing library is prepared from genomic DNA and target-specific oligonucleotides are synthesized and used to construct primer-probes on the flow cell. Then, immobilized primer-probes on the flow cell are used to capture single molecule targets from a single-adapter genomic DNA library.

Processing of OS-Seq involves three-step where the Illumina sequencing system is modified to contain target-specific primer-probes, targets are captured from a single-adapter library and immobilized fragments are finalized for sequencing (FIG. 1b), To prepare the capture substrate, we molecularly re-engineer the Illumina flow cell by modifying a subset of the existing primer lawn to become target-specific primer-probes. To create these primer-probes, we hybridize the 3' universal sequence of a complex pool of oligonucleotides to its complement on the flow cell and extend the immobilized primer using a DNA polymerase extension reaction. The result is a set of randomly placed, target-specific primer-probes, which are fixed onto the flow cell surface. During high-heat incubation at 65° C., the primer-probes specifically hybridize to target complementary sequences within the single-adapter genomic DNA library; after hybridization, the primer-probes then function as primers for another DNA polymerase extension reaction. The extension step effectively captures the target sequence. After extension, a denaturation step is performed followed by low-heat hybridization at 40° C. to stabilize the sequencing library adapter to its complement on the flow cell, which creates a bridge structure. A third DNA polymerase extension reaction incorporates additional sequence to the 3' ends, creating two molecules capable of solid phase amplification. After three steps specific to OS-Seq, captured molecules are bridge amplified, processed and sequenced using the standard sequencing protocol from the Illumina NGS system. A detailed description of the molecular biology steps in OS-Seq is given in above and the Illumina cluster station programs for OS-Seq is modified accordingly.

Figure 4:
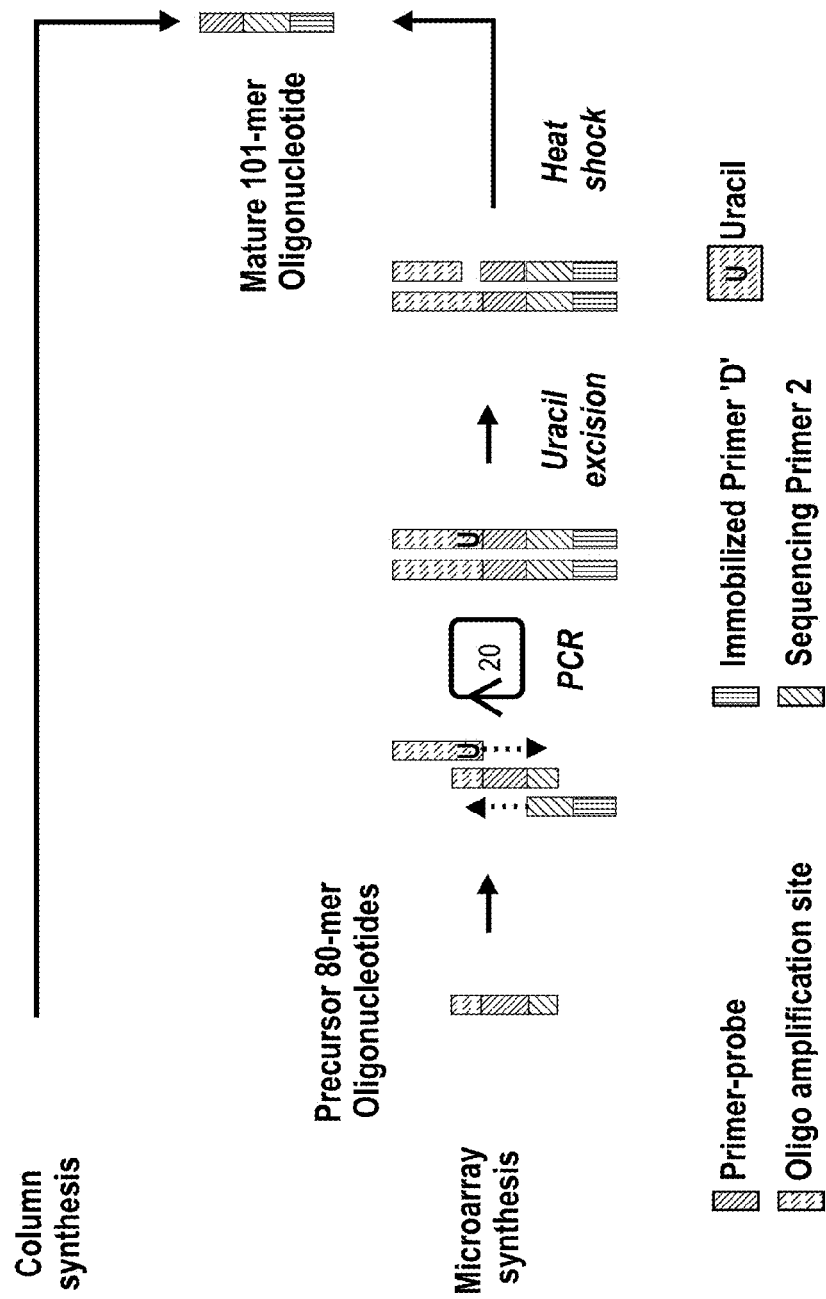
FIG. 4. Generation of OS-Seq oligonucleotides. Column-synthesis yielded large amount of mature 101-mer OS-Seq oligonucleotides that were readily usable in the assay. Microarray-synthesis was applied to generate high-content oligonucleotide pools. Precursor oligonucleotides were amplified using primers that incorporated additional sequences into oligonucleotides. Uracil-excision was applied to cleave the amplification primer site from the coding strands of the OS-seq oligonucleotides.

As a proof-of-principle demonstration, two capture assays were developed. First, 366 OS-Seq primer-probes to flank the exons of 10 cancer genes (OS-Seq-366) were designed (FIG. 3). This assay was intended to test the OS-Seq method and not for definitive exon coverage. We synthesized OS-Seq-366 oligonucleotides using column-based methods. Second, to demonstrate scalability, we designed and synthesized 11,742 primer-probes to capture the exons of 344 cancer genes (OS-Seq-11k). These primer-probes avoided repeats and were tiled across large exons for improved exon coverage. For high-throughput production of OS-Seq-11k, we synthesized the oligonucleotides on a programmable microarray. These array-synthesized oligonucleotides require amplification for processing and for obtaining sufficient material for OS-Seq (FIG. 4). Post-processed, OS-Seq oligonucleotides contain a target-specific 40-mer complementary to the 5' end of the targeted region (FIG. 5). These oligonucleotides also contain sequence required for annealing the paired-end sequencing primer and for hybridization to the immobilized primer lawn on the flow cell.

To assess capture performance of the OS-Seq-366 and OS-Seq11k assays, DNA from a previously sequenced Yoruban individual was prepared (NA18507). Paired-end sequencing was conducted on all targeting assays. The first read (Read 1) is derived from targeted genomic DNA while the second read (Read 2) comes from the synthetic target-specific primer-probes (FIG. 1a). OS-Seq-366 was run on a single lane of a GAIIx run. Each sample of OS-Seq-11k was run on the equivalent of 1.3 lanes, based on our indexing scheme. We developed an indexing scheme using adapters with a unique barcode sequence (FIG. 5c) to tag samples. Barcodes were derived from the first seven bases of Read 1. Overall, 87.6% of OS-Seq-366 reads and 91.3% of OS-Seq-11k reads, containing proper barcodes, mapped to the human genome reference (Table 1). In comparison, 58% of reads derived using a previously reported hybrid selection method could be mapped to the human genome reference.

TABLE 1

| Sample | NA18507 | NA18507 | Normal | Tumor |
| --- | --- | --- | --- | --- |
| Number of primer-probes | 366 | 11,742 | 11,742 | 11,742 |
| Total reads | 1,969,091 | 1,602,825 | 2,038,270 | 1,551,279 |
| Mapped reads | 1,725,215 | 1,463,782 | 1,897,967 | 1,415,388 |
| (percentage of total reads) | (87.6%) | (91.3%) | (93.1%) | (91.2%) |
| Captured on-target reads[a] | 1,499,052 | 1,365,305 | 1,747,192 | 1,316,563 |
| (percentage of mapped reads) | (86.9%) | (93.3%) | (92.1%) | (93.0%) |
| Captured on-target exon reads[b] | 518,318 | 624,937 | 725,072 | 608,458 |
| (percentage of mapped reads) | (30.0%) | (42.7%) | (38.2%) | (43.0%) |
| Captured off-target reads | 226,163 | 98,477 | 150,775 | 98,825 |
| (percentage of mapped reads) | (13.1%) | (6.7%) | (7.9%) | (7.0%) |
| On-target region[a] | 233 kb | 7,296 kb | 7,296 kb | 7,296 kb |
| Captured on-target region used for SNV calling[a,c] | 191 kb | 1,541 kb | 1,754 kb | 1,476 kb |
| (percentage of on-target region) | (82.0%) | (21.1%) | (24.0%) | (20.2%) |
| OS-Seq SNVs called from captured on-target region | 105 | 985 | 871 | 727 |
| OS-Seq SNPs which are reported | 97%[d] | 95.7%[d] | — | — |
| OS-Seq SNPS which concordant with array genotype | — | — | 99.8%[e] | 99.5%[e] |
| Exon regions[b] | 31 kb | 959 kb | 959 kb | 959 kb |
| Captured exon regions[b,f] | 26 kb | 917 kb | 901 kb | 909 kb |
| (percentage of exon regions) | (83.9%) | (95.6%) | (94.0%) | (94.8%) |
| Average fold-coverage on captured exons[b,f] | 729 | 31 | 38 | 31 |

[a]Within 1 kb from primer-probes.
[b]Within exons.
[c]Filtered insert size ≥40 + read 1 length. Fold-coverage ≥10. Phred-like quality score >50.
[d]Merged variant bases from Bentley et al. (2008) and dbSNP131.
[e]Positions genotyped using Affymetrix SNP 6.0 arrays.
[f]Fold-coverage ≥1.

Figure 6:
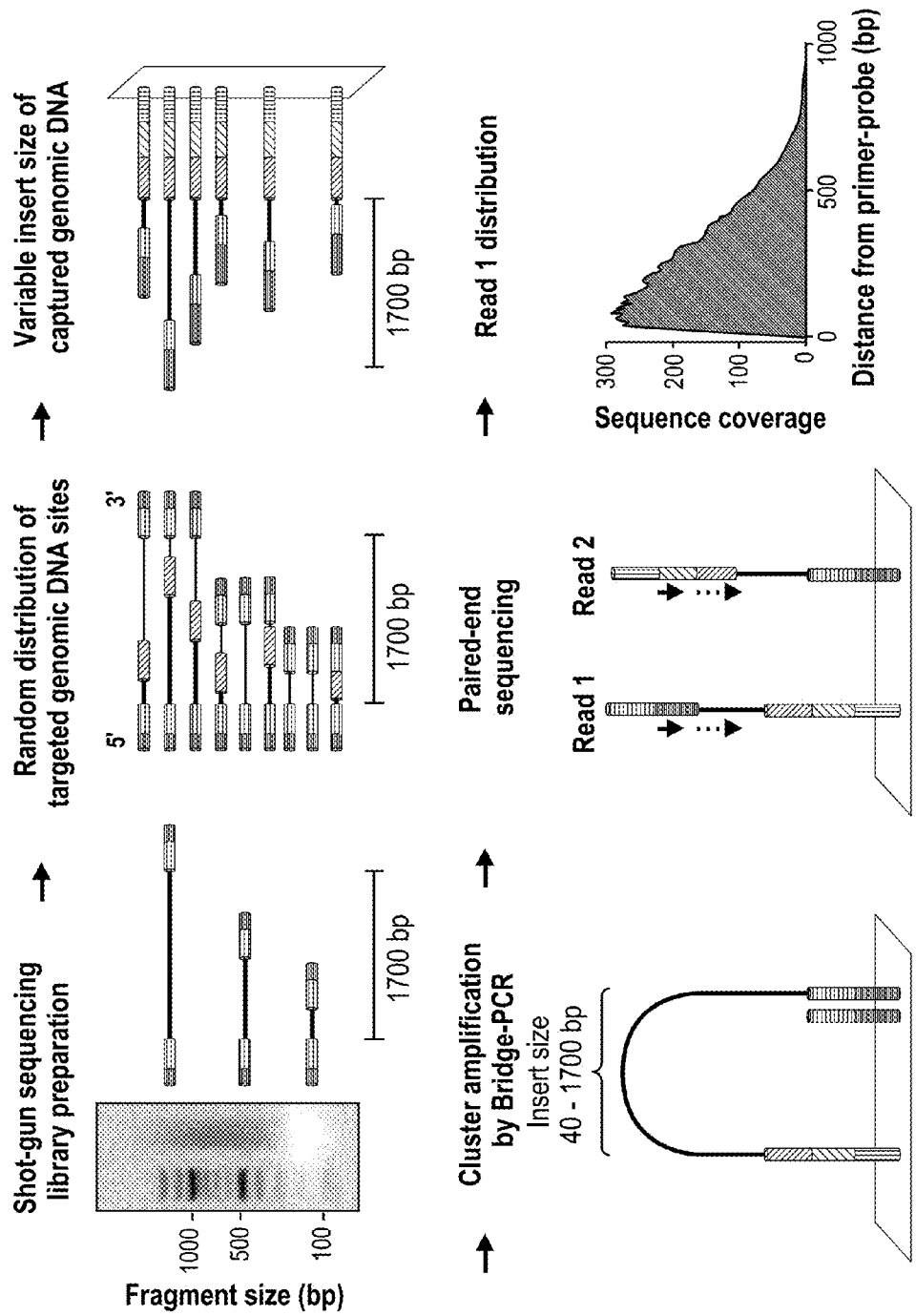
FIG. 6. Description of insert size distributions encountered in OS-Seq data. Fragmentation of genomic DNA produces fragments between 200 and 2 kb. Sequencing library preparation adds common adapter to the ends of the fragments. PCR amplification distorts the fragment size distribution further. Target sites are randomly distributed within the single-adapter library fragments. Library fragments were immobilized on the flow cell and the distance between primer-probe and adapter defined the size of a genomic DNA insert. Bridge-PCR is applied to amplify immobilized target DNA (generally, solid-phase PCR preferentially amplifies shorter fragments). After cluster amplification and processing, immobilized fragments are sequenced using two sites. Read 1 originates from the genomic DNA and Read 2 is derived from the synthetic primer-probes. Read 1 is used for assessing the genomic DNA sequence from OS-Seq data.

To assess overall coverage of each primer-probe, we determined the number of reads originating from the Read 1 data that fell within 1 kb from the 3' end of the primer-probe. OS-Seq primer-probes are strand-specific and only capture the 5' ends of the DNA targets (FIG. 6). As an example, the median coverage profile of all primer-probes in OS-Seq-366 (FIG. 1a) illustrates how sequence is captured up to 1 kb downstream from the primer-probe. Generally, a bias towards smaller insert sizes was detected, for OS-Seq-366 50% of targeted reads mapped within 283 bases from the primer-probes. In both assays, additional reads beyond the 1 kb interval and as far distant as 1.7 kb were identified. The sequence reads beyond 1 kb represent the tail end of the capture distribution from any given primer-probe and was less than 0.15% of the overall sequence data for both OS-Seq-366 and OS-Seq-11k. It was also observed that the characteristics of the coverage distribution is correlated with the fragment size introduced during library creation and from size constraints inherent to bridge-formation and solid-phase PCR (FIG. 6). Also, introducing a higher molar concentration of the single adapter library, sequencing additional lanes or using longer reads can increase coverage along the target.

On-target reads were defined as Read 1 sequences mapping within 1 kb of a primer-probe. Using these on-target coverage criteria, 86.9% of 40 base reads in OS-Seq-366 and 93.3% of 53 base reads in OS-Seq-11k were on-target (Table 1). OS-Seq-11k showed improved specificity given efforts to refine the in-silico design of the primer-probes. Specifically, for OS-Seq-11k in-silico primer-probe selection, a repeat masking filter was used, which resulted in fewer off-target reads. In comparison, 89% of 76 base reads and 50% of 36 base reads mapped in proximity of a probe in a published hybrid selection method, suggesting similar on-target specificity between methods and inclining that moving towards longer reads may improve the on-target specificity of OS-Seq. On-exon specificity of OS-Seq was also similar to the published hybrid selection method. Using OS-Seq-11K, we observed that 42.7% of reads mapped within exons (Table 1), while a hybrid selection capture technology reported 42% of reads mapped to exons.

Figure 1C:
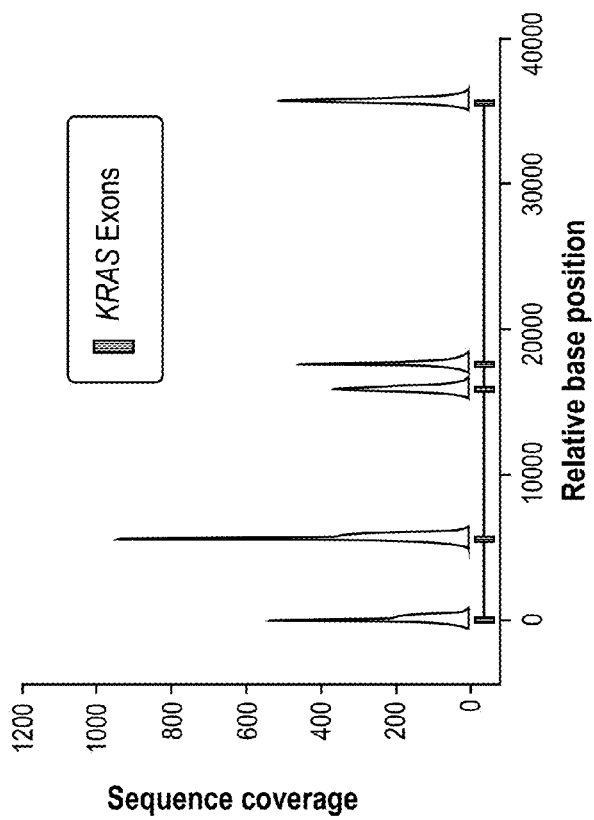

As an example of a typical gene coverage profile, we show the captured sequence data for the KRAS gene in FIG. 1c. The exon targets are sequenced at high fold-coverage relative to the off-target adjacent regions. As noted previously, OS-Seq-366 was designed to flank exons and did not tile across large regions. The average fold coverage for exons in Table 1 and detailed breakdowns of coverage classes (i.e. 10×, 20×) in Table 2. Overall, 83.9% of exon bases in the OS-Seq-366 were covered with at least one read, with a portion of the remainder not having been intentionally targeted in this pilot assay. Similarly, among the three samples analyzed with OS-Seq-11k, 94 to 95.6% of exon bases were covered with at least one read. Compared to OS-Seq-366, the OS-Seq-11k assay showed increased sequence coverage on exons due to an improvement of the primer-probe design over the OS-Seq-366 design, specifically, the OS-Seq-11k design tiled primer-probes across exons larger than 500 bases.

Also evaluated was the assay's target selection uniformity by binning Read 1 data by its associated primer-probe and counting reads aligning to its target. OS-Seq primer-probes were sorted based on the observed capture yields and the distributions within OS-Seq-366 and OS-Seq-11k are presented in an overlay fashion in FIG. 1d. In OS-Seq-366, it was observed observed that 100% of the primer-probes had a yield minimum of one sequence read and the yield of 89.6% of the primer-probes were within a 10-fold range. Similarly, for OS-Seq-11k, 95.7% of primer-probes had a capture yield minimum of one sequence read and 54% of the primer-probes had a yield within a 10-fold range. OS-Seq-366 oligonucleotides were column-synthesized and quantified separately prior to pooling, which ensured that each target-specific sequence was in equimolar concentration in the primer-probe construction step. Higher variance in primer-probe yields for OS-Seq-11k is most likely attributed to amplification bias introduced during PCR of the microarray-synthesized oligonucleotides used for primer-probe creation.

Figure 7A:
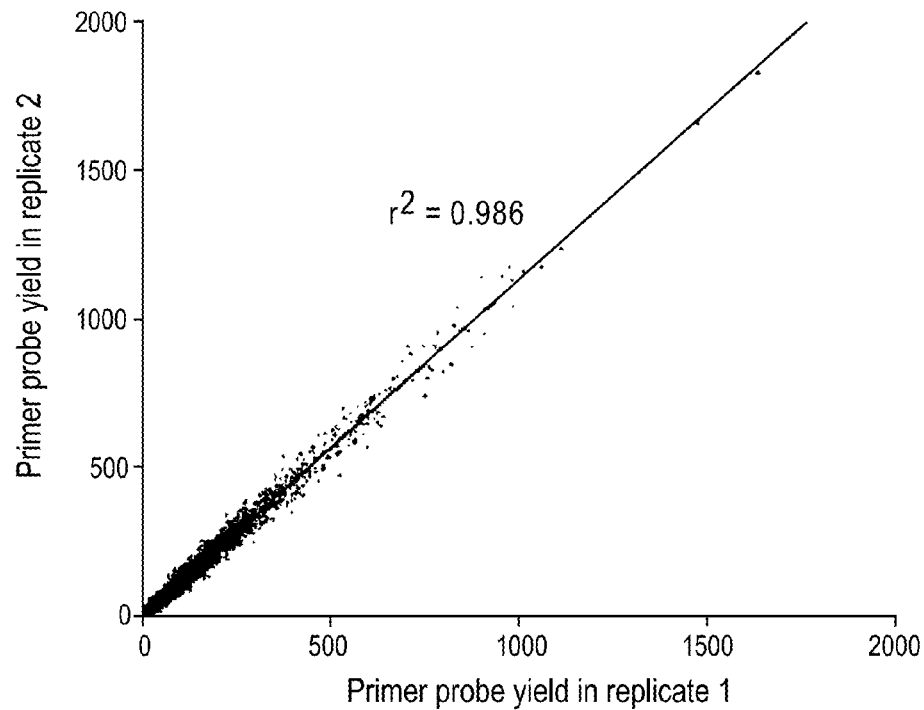
FIG. 7. Reproducibility of OS-Seq. (a) Technical reproducibility of OS-Seq. Two identical libraries were analyzed using OS-Seq. Sequencing yields of individual primer-probes were compared between technical replicates. (b) Biological reproducibility of OS-Seq. Two different genomic DNA libraries were prepared using indexed adapters. Libraries were analyzed in the same OS-Seq experiment. In the figure, primer-probe specific capture yields are compared between two independent biological replicates.
Figure 7B:
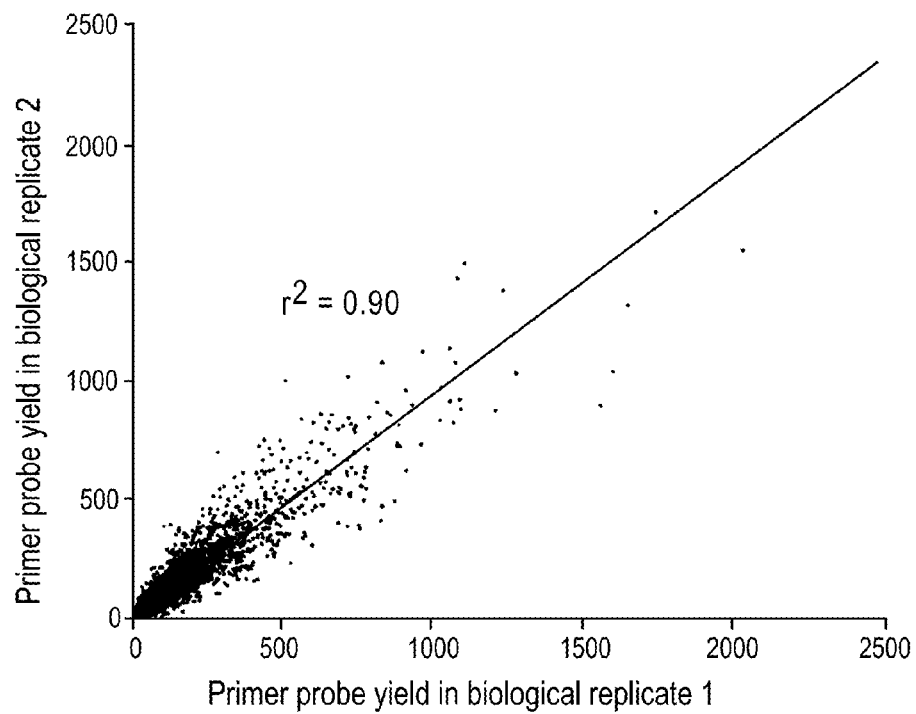

The technical reproducibility of OS-Seq was evaluated by comparing the sequence yields of individual primer-probes from the OS-Seq-11k assay (FIG. 7). Multiplexed libraries (NA18507, normal and tumor) were pooled and the capture and sequencing was performed on two independent Illumina GAIIx lanes. The sequence yields of each individual primer-probe was compared between the technical replicates and calculated the correlation coefficient: $R^2=0.986$. For evaluation of biological reproducibility, two different multiplexed sequencing libraries were run in the same lane. The correlation coefficient of biological replicates was $R^2=0.90$. High reproducibility of OS-Seq is likely to be related to the inherent automation using the NGS system, the ability to perform the capture and sequencing steps in a single reaction volume and not having to apply post-capture PCR.

To assess the variant calling performance of OS-Seq-366 and OS-Seq-11k assays, a targeted sequencing analysis on NA18507, a Yoruban individual who has undergone complete genome sequencing analysis, was conducted. For SNV calling with either OS-Seq assay, we analyzed only on-target positions with genotype quality scores greater than 50 and a minimum of 10× coverage (Table 1). For OS-Seq-366 and OS-Seq-11k data, a total of 191 kb and 1,541 kb fulfilled these criteria, respectively. From these high quality, targeted positions, we called 105 SNVs from OS-Seq-336 and 985 SNVs from OS-Seq-11k (Table 1). We extracted the published NA18507 SNVs and other reported SNPs that occurred in these same high quality regions. In comparison, 97% of the OS-Seq-366 and 95.7% of the OS-Seq-11k had previously been reported (Table 1). For OS-Seq-366 and OS-Seq-11k the sensitivity of variant detection was 0.97 and 0.95 respectively based on the reported SNPs (Table 3 below).

TABLE 3

| Sample | 18507 | 18507 |
|---|---|---|
| Reported SNP data | Bentley et al. (2008) and dnSNP131 | Bentley et al. (2008) and dnSNP131 |
| OS-Seq assay | OS-Seq-366 | OS-Seq-11K |
| Total OS-Seq SNVs | 105 | 985 |
| OS-Seq SNVs concordant with reported SNP position | 105 | 943 |
| OS-Seq SNVs not reported elsewhere | — | 42 |
| Reported NA18507 SNPs not called by OS-Seq | 3 | 54 |
| OS-Seq SNV Sensitivity | 0.968 | 0.947 |

OS-Seq-11k analysis was also applied to genomic DNA derived from a matched normal—colorectal carcinoma tumor pair. Using the same quality and coverage criteria for the analysis of NA18507, identified 871 SNVs were identified from the normal sample and 727 from the tumor (Table 4). For comparison, the two samples with the Affymetrix SNP 6.0 array were genoyped. According to previous analyses, genotyping accuracy using Affymetrix SNP 6.0 arrays and the Birdseed algorithm is high, as the average successful call rate for SNPs is 99.47% and called SNPs have a 99.74% concordance with HapMap genotypes from other platforms. In comparing the OS-Seq SNVs to Affymetrix SNPs, a high concordance of 99.8% for the normal and 99.5% for the tumor was observed. By filtering normal tissue variants and considering novel cancer-specific variants where coverage was greater than 40, a clear pathogenic nonsense mutation of SMAD4 (S144*) was identified and validated. This gene is frequently mutated in colorectal cancer and a colon cancer driver gene.

TABLE 4

| Sample | 2722A | 2736A |
|---|---|---|
| Source of array SNP data | Affymetrix SNP 6.0 | Affymetrix SNP 6.0 |
| OS-Seq assay | OS-Seq-11K | OS-Seq-11K |
| Total OS-Seq SNVs | 871 | 727 |
| OS-Seq SNVs concordant with array SNPs | 546 | 418 |
| Array SNPs not called by OS-Seq | 1 | 2 |

Figure 8A:
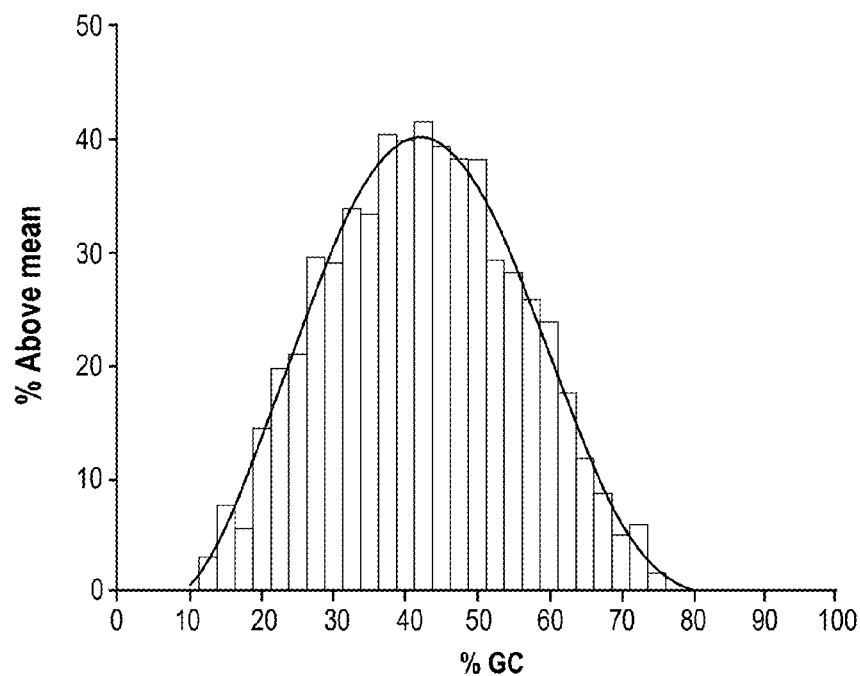
FIG. 8A-B. Effect of GC content on targeting yield. To analyze the effect of GC content in the efficiency of primer-probes, we determined the GC content of each target-specific primer-probe sequence. We classified primer-probes that were failing (captured 0 targets). Proportions of failing primer-probes were compared between different % CG content categories. X-axis presents the percentages of the sorted CG categories and y-axis reports the proportion of failed primer-probes within each GC content category.
Figure 8B:
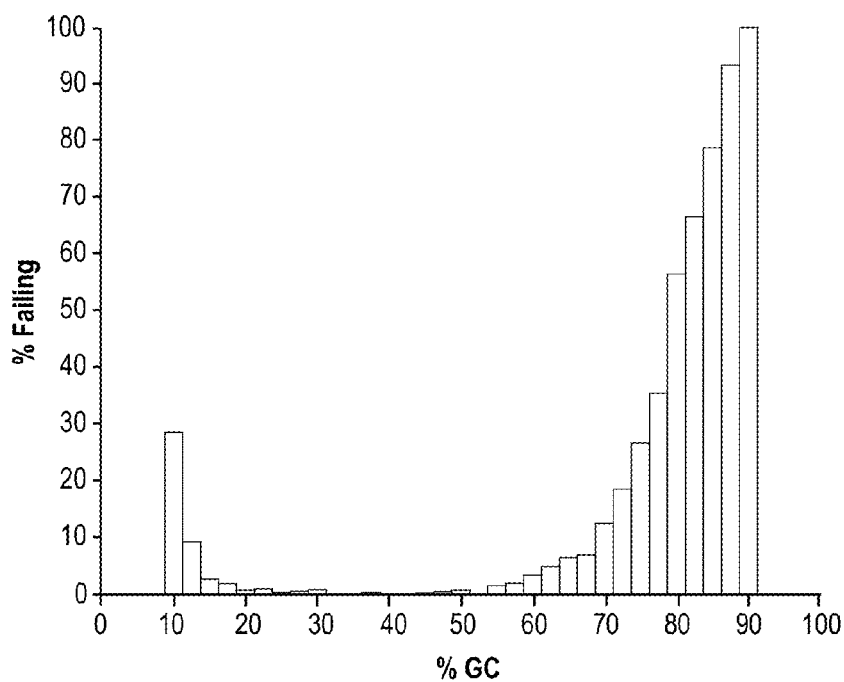

The capture efficiency of individual primer-probes within the OS-Seq-366 and OS-Seq-11k assays was investigated, and the performance of each primer-probe was assessed. A unique feature of OS-Seq is that captured genomic sequences can be matched to their corresponding primer-probes when sequenced with paired-ends. Read 1 originates from the 3' end of the captured target and Read 2 begins at the OS-Seq primer-probe synthetic sequence. Thus, Read 1 always represents the captured genomic DNA sequence while Read 2 functionally serves as a molecular barcode for a distinct primer-probe. This enables the identification of the exact OS-Seq primer-probe, which mediated the targeting, and facilitates the assessment of the performance of individual primer-probes. For example, we observed a strong relationship between primer-probe GC content and target sequence yield (data not shown). Extremely low GC (less than 20%) or high GC content (>70%) was associated with increasing failure of a primer-probe to capture its target sequence (FIG. 8). It is believed that that the ability to directly evaluate the capture performance will be a useful primer-probe quality control measure.

The OS-Seq technology was developed for streamlined and highly scalable targeted resequencing. A departure from the traditional capture methods of pre-sequencing target enrichment, OS-Seq integrates capture and sequencing of the target DNA via hybridization and selection on the solid phase support of a NGS system. This proof-of-principle study shows that the OS-Seq assay effectively and reproducibly captures target genomic regions with good uniformity and high specificity. Variant analysis of the NA18507 reference genome demonstrated high specificity and low false discovery rate for SNV determination. Targeted resequencing of matched colorectal tumor and normal samples demonstrated the applicability of OS-Seq to high-throughput genetic analysis of cancer genomes.

The OS-Seq technology enables one to create custom targeted resequencing assays. The design and production of the primer-probe oligonucleotides is relatively straightforward and target regions can be selected simply by using balanced GC and non-repetitive sequence. Programmable microarray synthesis resources can be used to generate customized and complex oligonucleotide libraries en masse. Likewise, traditional oligonucleotide synthesis methods can be used to create customized assays for smaller target gene sets. While our largest targeting assay covered the exons and adjacent sequence of 344 genes, we believe that OS-Seq can be significantly scaled up to larger target contents. From the OS-Seq-366 data we estimated that there was over 2,000-fold excess of primer-probes compared to target fragments in the hybridization mix inside the flow cell. During 20-hour hybridization, we estimate that 4.9% of all potential targets within the library were captured for sequencing. We have also tested that the concentration of oligonucleotides can be increased at least 10-fold and the concentration of the sequencing library can be increased 5-fold (data not shown) without compromising cluster formation.

The OS-Seq sample preparation is straightforward: it can be completed in one day and is readily automated (FIG. 9). In regard to labor, using OS-Seq compares favorably to executing a shotgun sequencing experiment. Because residual adapters are not hybridizing to the flow cell during capture, OS-Seq libraries can use DNA fragments of varying sizes without the necessity of narrow size purification by physical separation methods. Only a single adapter needs to be added to the 5' ends of a genomic DNA fragment. The single-adapter design also readily lends itself to indexing with introduction of a molecular barcode. This feature allows straightforward sample multiplexing of sequencing assays and has many potential applications. For example, matched normal tumor analysis occurs in the same capture reaction, which may reduce biases.

Given the increasing interest in "personalized medicine" there is a clear need to develop rapid and simple approaches to human genome resequencing. This includes the analysis of germline variants and the somatic mutations found in cancer genomes. As a practical and efficient approach for targeted resequencing, OS-Seq is particularly useful for translational studies and clinical diagnostics by enabling high-throughput analysis of candidate genes and identification of clinically actionable target regions.

For the method described above, an Illumina Genome Analyzer was used. However, it is anticipated that this system will be broadly applicable to any parallel sequencing platform.

What is claimed is:

1. A method of capturing and amplifying a selected sequence comprising:
   a) obtaining a substrate comprising a first population of surface-bound oligonucleotides and a second population of surface-bound oligonucleotides, wherein the members of said first and second populations of surface-bound oligonucleotides are attached to the same substrate but not spatially addressed on said substrate;
   b) hybridizing a first member of said first population of surface-bound oligonucleotides to a selection oligonucleotide comprising a region that hybridizes with said first member and a region that contains a genomic sequence,
   c) extending said first member of said first population of surface-bound oligonucleotides using the hybridized selection oligonucleotide of (b) as a template to produce an extended support-bound selection primer that comprises a sequence that is complementary to said genomic sequence;
   d) hybridizing said extended support-bound selection primer of step c) to denatured fragmented genomic DNA to produce a duplex comprising said extended support-bound selection primer and a strand of genomic DNA that comprises said genomic sequence, wherein, in the duplex, the strand of genomic DNA is at least 100 bases in length and the 3' end of the extended support-bound selection primer is extendible using the strand of genomic DNA as a template;
   e) extending said extended support-bound selection primer using the strand of genomic DNA as a template to produce an extension product that contains the complement of a sequence that flanks said genomic sequence; and
   f) amplifying said extension product of step e) on said substrate by bridge PCR using unextended members of said first and second populations of surface-bound oligonucleotides of step a), to produce a PCR product.

2. The method of claim 1, wherein said strand of genomic DNA is comprises a 5' end adaptor, wherein said extending of step e) produces an extension product that comprises, on its 3' end, a sequence that is complementary to said adaptor, and wherein members of said second population of said surface-bound oligonucleotides hybridize to said sequence that is complementary to said adaptor during said amplifying step f).

3. The method of claim 2, wherein said 5' end adaptor comprises a binding site for a sequencing primer.

4. The method of claim 1, wherein said method comprises, between steps e) and f), ligating an adaptor onto the 3' end of said extension product, and wherein members of said second population of said surface-bound oligonucleotides hybridize to said adaptor during said amplifying.

5. The method of claim 4, wherein said adaptor comprises a binding site for a sequencing primer at the end that is ligated to said extension product.

6. The method of claim 1, wherein said second population of surface-bound oligonucleotides are made by:
   i. hybridizing members of an initial second population of surface-bound oligonucleotides to an oligonucleotide comprising a region that hybridizes with the members of said second population of surface-bound oligonucleotides and a region that is complementary to a sequence of said strand of genomic DNA; and
   ii. extending said members of said initial second population of surface-bound oligonucleotides to produce said second population of surface-bound oligonucleotides.

7. The method of claim 1, wherein said selection oligonucleotide comprises a binding site for a sequencing primer between said region that hybridizes with said first member and said region that contains said genomic sequence.

8. The method of claim 1, further comprising sequencing a first strand of said PCR product to obtain at least part of the nucleotide sequence of said sequence that flanks said genomic sequence, or complement thereof.

9. The method of claim 1, further comprising sequencing the second strand of said PCR product to obtain at least part of the nucleotide sequence of said sequence that flanks said genomic sequence, or complement thereof.

10. The method of claim 1, wherein said method comprises fragmenting a mammalian genome to produce a fragmented genome, optionally adding adaptors to said fragmented genome, and applying said fragmented genome to said substrate.

11. The method of claim 10, wherein said fragmenting is done physically, chemically or using a restriction enzyme.

12. The method of claim 11, wherein said fragmenting is done by sonication or shearing.

13. The method of claim 10, wherein said hybridizing is done by preparing a plurality of fragmented genomes from a plurality of different individuals, pooling said plurality of fragmented genomes to produce a pool, applying said pool of fragmented genomes to said substrate, and obtaining PCR products that comprise a sequence that flanks said genomic sequence in said different individuals.

14. The method of claim 13, further comprising sequencing at least the first strand of said PCR products to obtain at least part of the nucleotide sequence of said sequence that flanks said genomic sequence in said different individuals.

15. The method of claim 14, wherein, prior to pooling, different adaptors are ligated to said fragmented genomes from said different individuals, wherein said the adaptor comprises a barcode sequence that allows the source of a sequence to be identified.

16. The method of claim 15, wherein said method comprises:
   adaptor-ligating fragmented genomic DNA from a first subject using a first adaptor that comprises a first barcode sequence to produce a first product;
   adaptor-ligating fragmented genomic DNA from a second subject using a second adaptor that comprises a second barcode sequence to produce a second product;
   combining said first and second products to produce a mixed template; and
   performing the method of claim 1 using said mixed template to provide first and second PCR product each containing said barcode sequence.

17. The method of claim 16, wherein said mixed template comprises fragmented genomic DNA from at least 1,000 subjects.

18. The method of claim 1, comprising:
   i. ligating the fragmented genomic DNA to an adaptor that contains a site for a sequencing primer and a nucleotide sequence that is the same as the second surface bound oligonucleotides,
   ii. hybridizing the adaptor-ligated fragments to a first member of the first population of surface-bound oligonucleotides,
   iii. extending the first member of the first population of surface-bound oligonucleotides to which the adaptor ligated fragment is hybridized; and
   iv. hybridizing the adaptor-containing end of the extension product to a second support bound polynucleotide, thereby producing a bridge and facilitating bridge PCR.

19. The method of claim 1, wherein said second population of surface-bound oligonucleotides are made by ligating an oligonucleotide comprising a region that is complementary to a sequence of said strand of genomic DNA to an initial second population of surface-bound oligonucleotides to produce said second population of surface-bound oligonucleotides.

20. A method of capturing and amplifying a selected sequence comprising the following steps, in order:
   a) obtaining a substrate comprising a first population of surface-bound oligonucleotides and a second population of surface-bound oligonucleotides, wherein the members of said first and second populations of surface-bound oligonucleotides are attached to the same substrate but not spatially addressed on said substrate;
   b) hybridizing a first member of said first population of surface-bound oligonucleotides to a synthetically-made selection oligonucleotide comprising a region that hybridizes with said first member and a region that contains a genomic sequence,
   c) extending said first member of said first population of surface-bound oligonucleotides using the hybridized synthetically-made selection oligonucleotide of step b) as a template to produce an extended support-bound selection primer that comprises a sequence that is complementary to said genomic sequence;
   d) denaturing the extended selection oligonucleotide of step c) from the support-bound selection primer;
   e) hybridizing said extended support-bound selection primer after step d) to a denatured fragmented genome to produce a duplex comprising said extended support-bound selection primer and a strand of genomic DNA that comprises said genomic sequence, wherein, in the duplex, the strand of genomic DNA is at least 100 bases in length and the 3' end of the extended support-bound selection primer is extendible using the strand of genomic DNA as a template;
   f) extending said extended support-bound selection primer using the strand of genomic DNA as a template to produce an extension product that contains a flanking sequence, wherein the flanking sequence is complementary to a sequence that flanks said genomic sequence in the genome; and
   g) amplifying said extension product of step f) on said substrate by bridge PCR using unextended members of said first and second populations of surface-bound oligonucleotides of step a), to produce a PCR product that comprises the flanking sequence.

\* \* \* \* \*